(12) United States Patent
Sochor

(10) Patent No.: US 12,357,815 B2
(45) Date of Patent: Jul. 15, 2025

(54) DBS LEAD FIXATION DEVICES HAVING A CLAMP AND/OR PERIPHERAL LEAD RETENTION GROOVES

(71) Applicant: Jerzy Roman Sochor, Sunnyvale, CA (US)

(72) Inventor: Jerzy Roman Sochor, Sunnyvale, CA (US)

( * ) Notice: Subject to any disclaimer, the term of this patent is extended or adjusted under 35 U.S.C. 154(b) by 434 days.

(21) Appl. No.: 17/469,793

(22) Filed: Sep. 8, 2021

(65) Prior Publication Data

US 2023/0191118 A1     Jun. 22, 2023

(51) Int. Cl.
    *A61N 1/05*         (2006.01)

(52) U.S. Cl.
    CPC ......... *A61N 1/0539* (2013.01); *A61N 1/0534* (2013.01)

(58) Field of Classification Search
    CPC ............... A61N 1/0539; A61N 1/0534; A61N 1/36067; A61N 1/37514; A61N 1/37518
See application file for complete search history.

(56) References Cited

U.S. PATENT DOCUMENTS

| | | | |
|---|---|---|---|
| 2010/0023100 A1* | 1/2010 | Barker | A61F 2/2875 607/116 |
| 2013/0066431 A1* | 3/2013 | Funderburk | A61F 2/2875 623/17.19 |

* cited by examiner

*Primary Examiner* — Ankit D Tejani
*Assistant Examiner* — Joshua Brendon Solomon

(57) ABSTRACT

Lead fixation devices for mounting at a cranial burr hole and securing a medical lead implanted into a brain through the burr hole. One embodiment comprises a clamp having centrally disposed clamping walls activated by a plunger having actuating tabs. The clamping walls may be an integral part of a device base, or a separate part seated in a central opening of the base. The clamp is activated by pressing the actuating tabs of the plunger into apertures adjoining the clamping walls, which displaces the clamping walls to clamp the lead. Another embodiment comprises a base having a plurality of radial and peripheral lead retention grooves configured to securely retain a substantial segment of the lead at the exit from the burr hole. Still another embodiment comprises both a clamp and peripheral retention grooves to provide a dual fixation and strain relief of the lead within the lead fixation device.

27 Claims, 30 Drawing Sheets

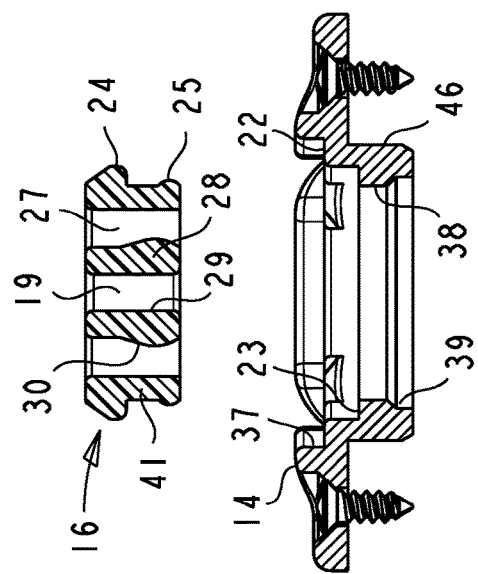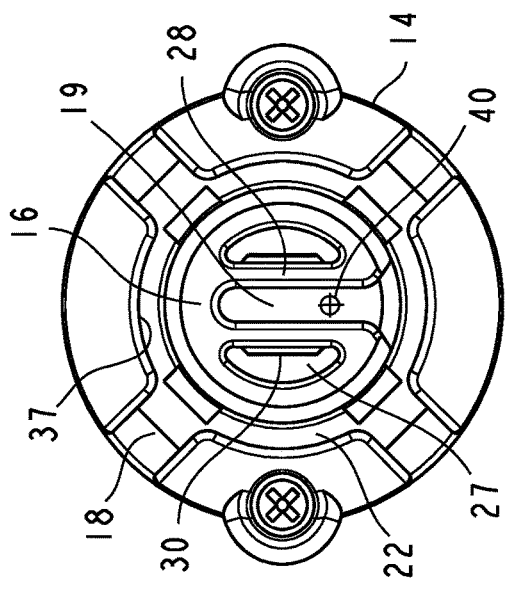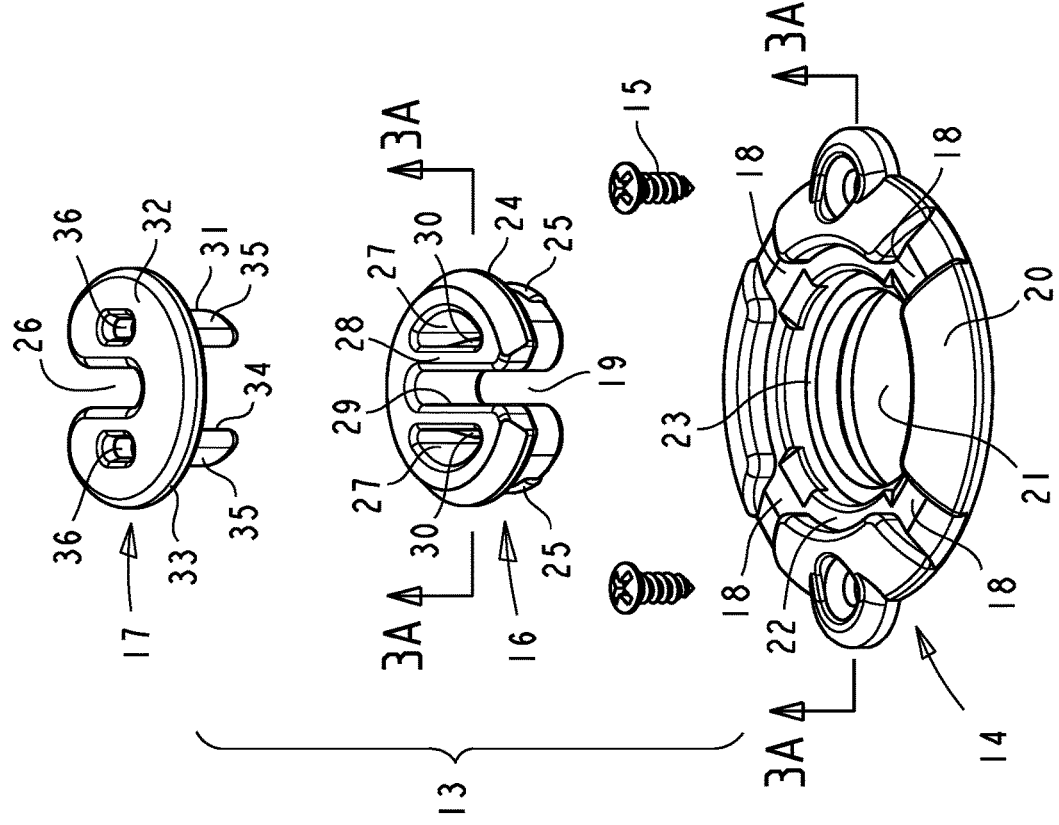

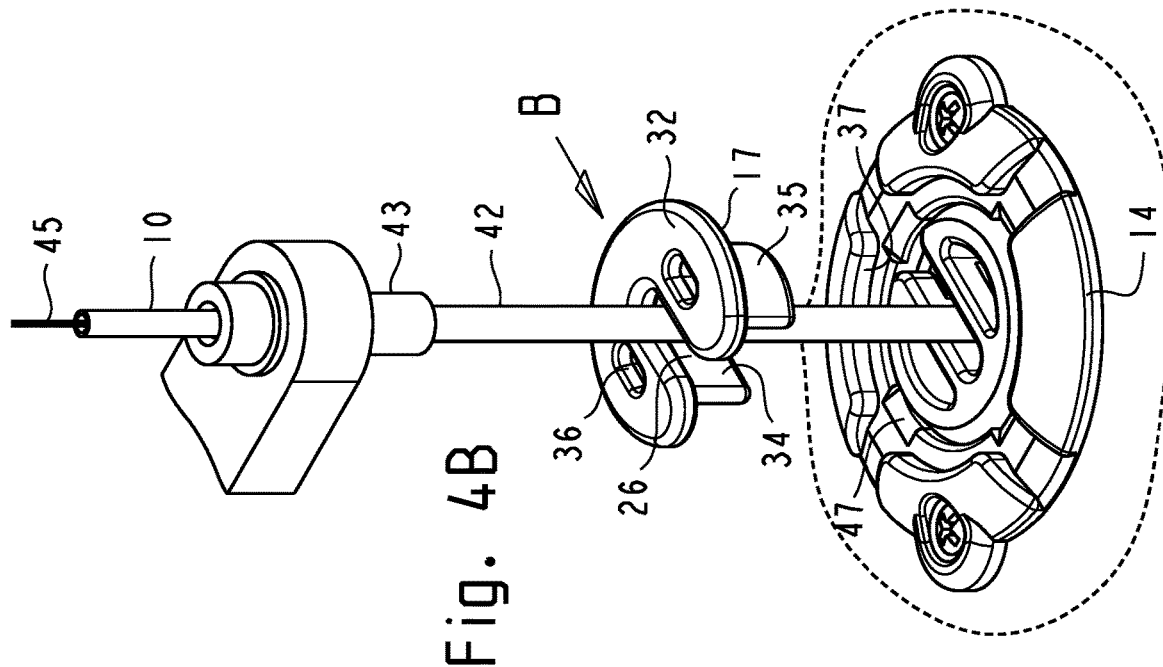
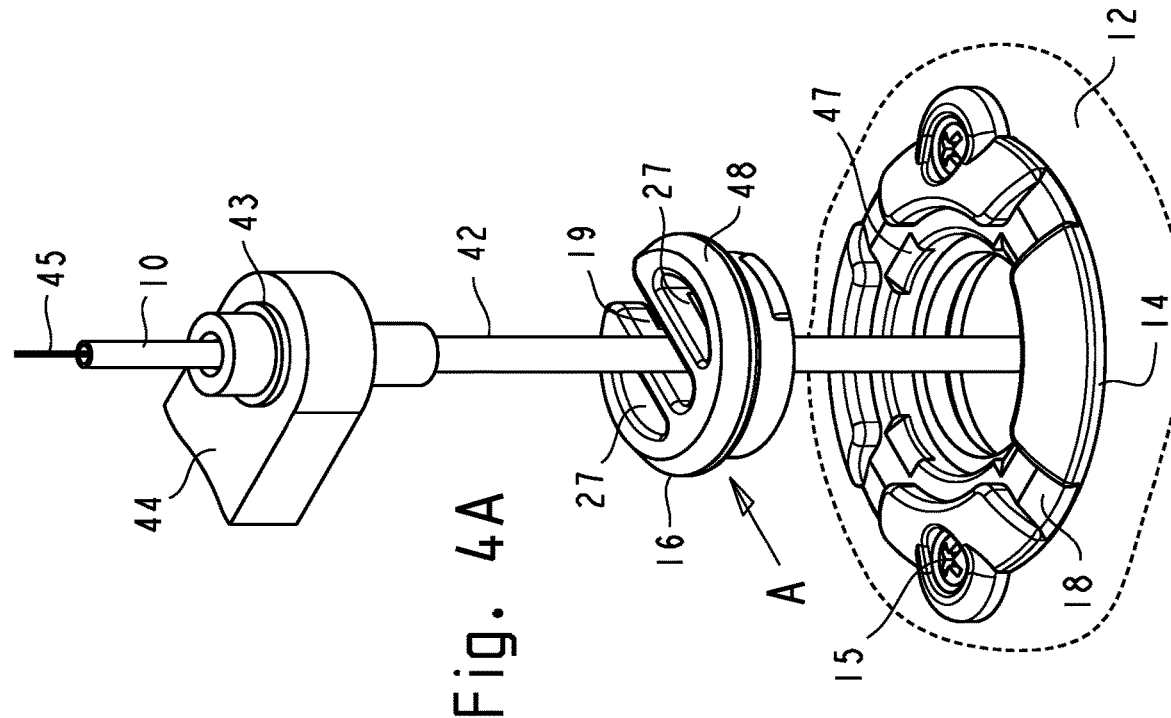

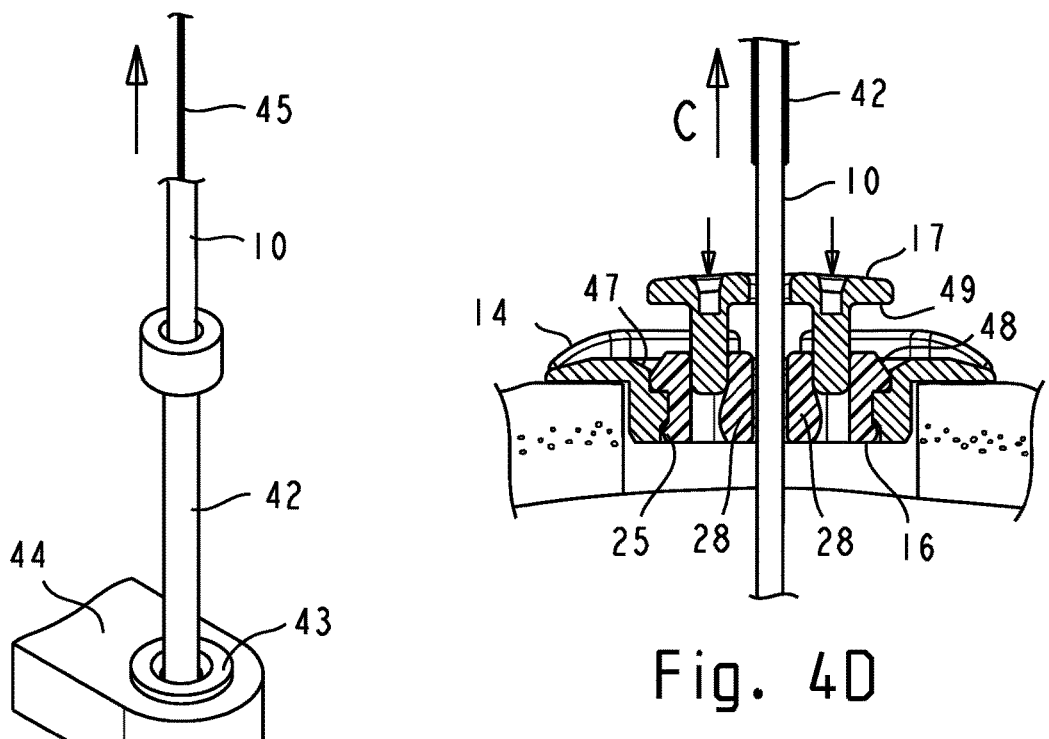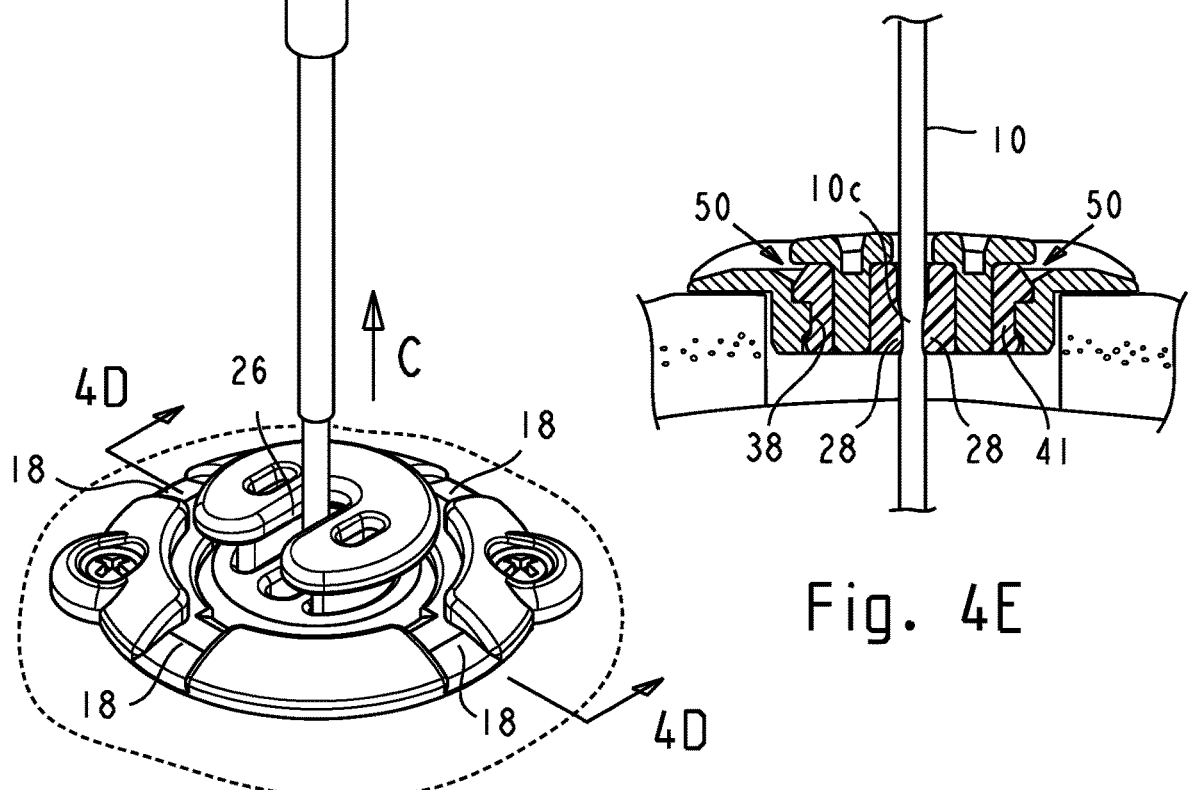

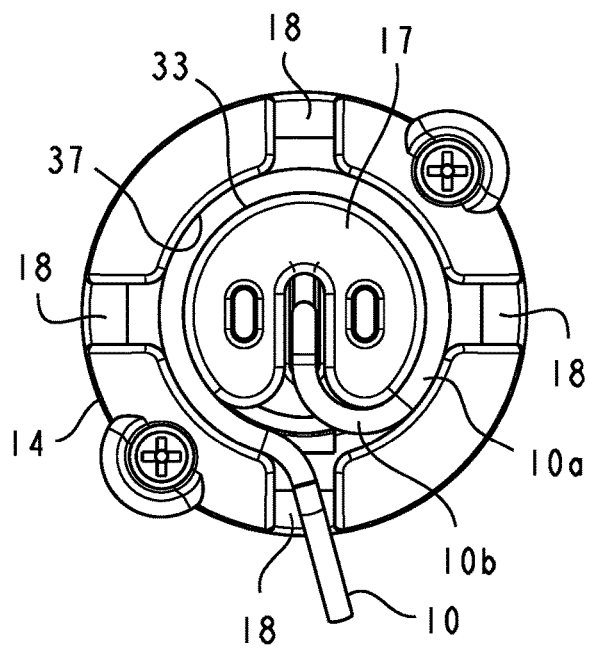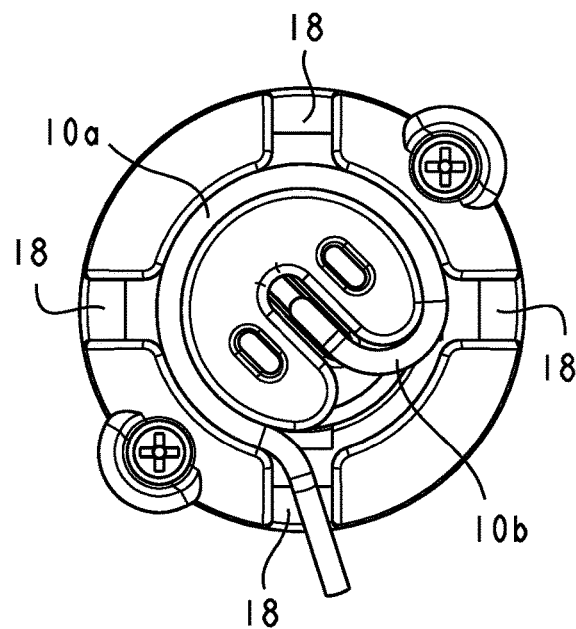
Fig. 5A  Fig. 5B
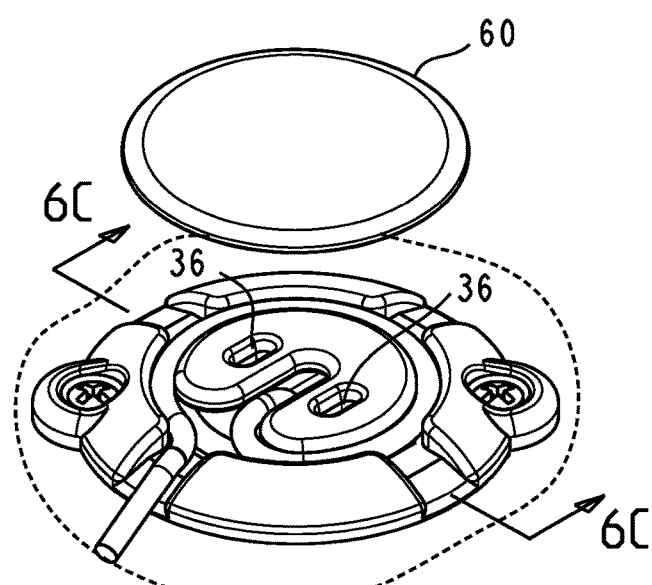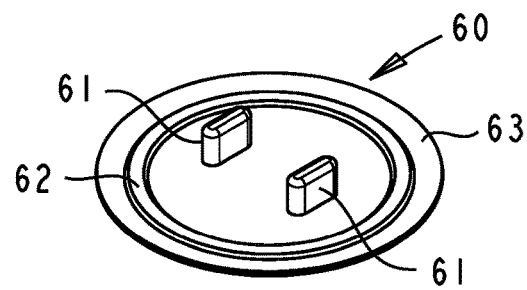
Fig. 6A  Fig. 6B
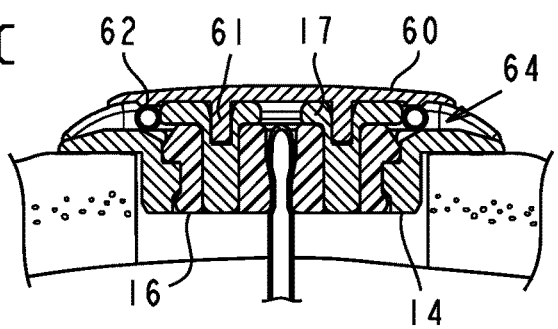
Fig. 6C

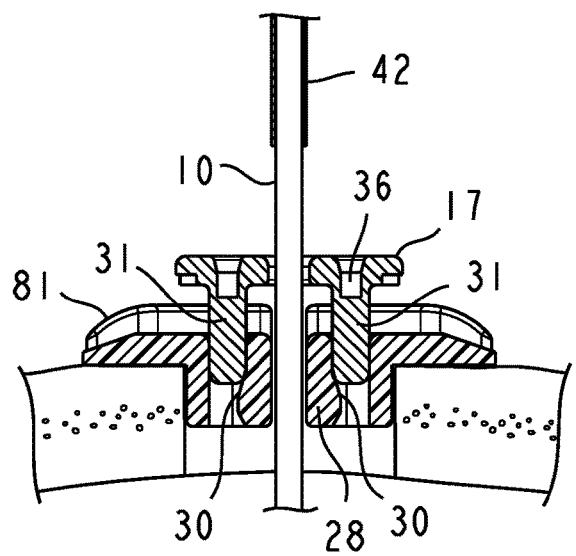
Fig. 9D
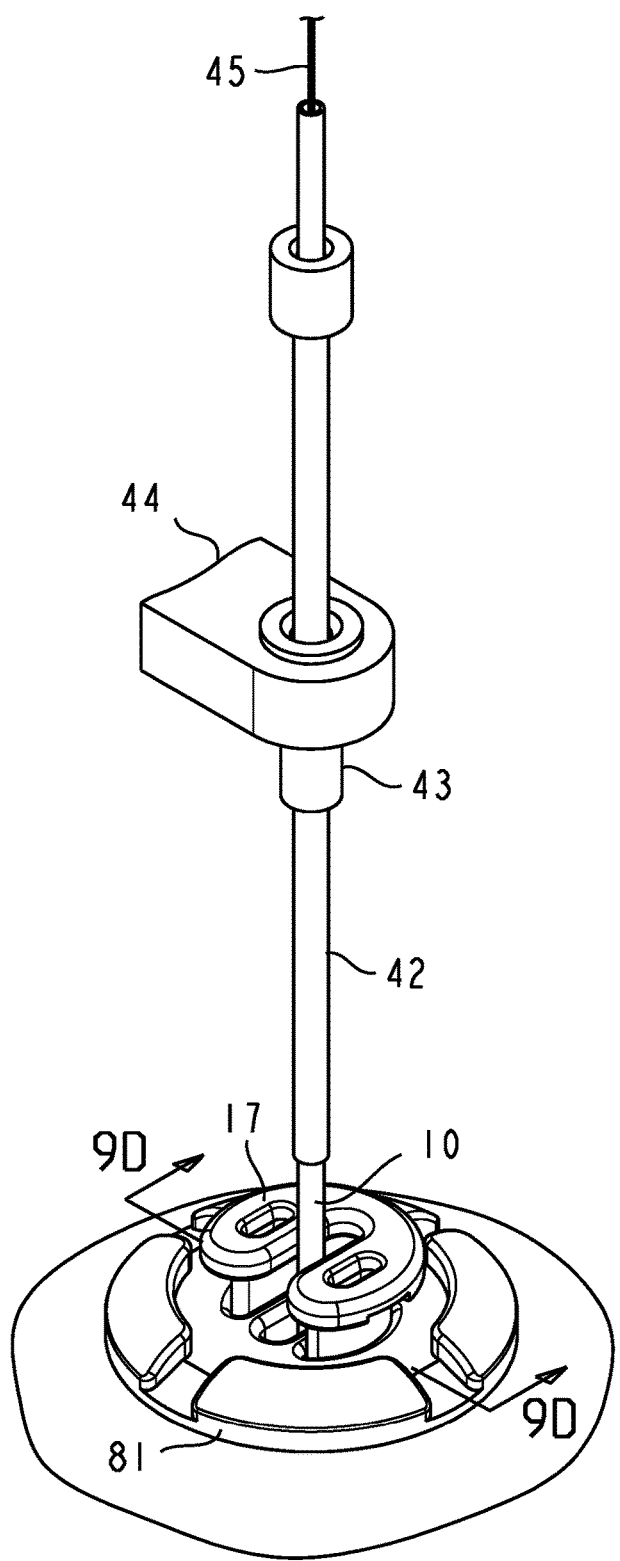
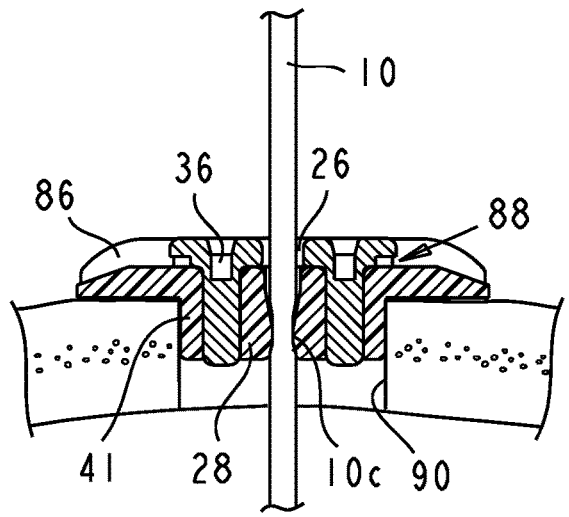
Fig. 9E
Fig. 9C

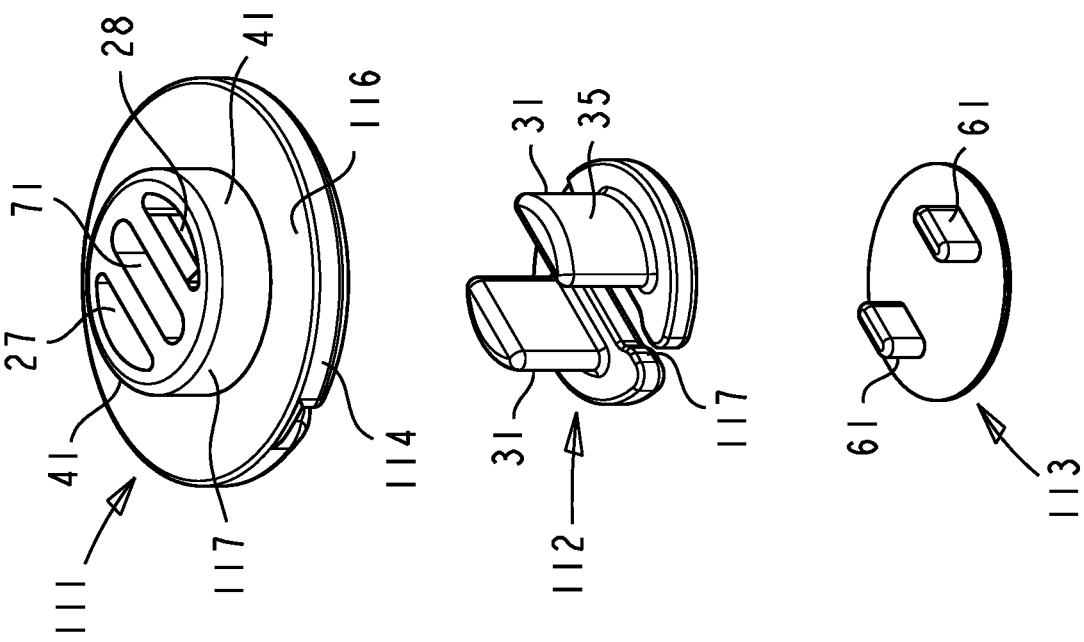
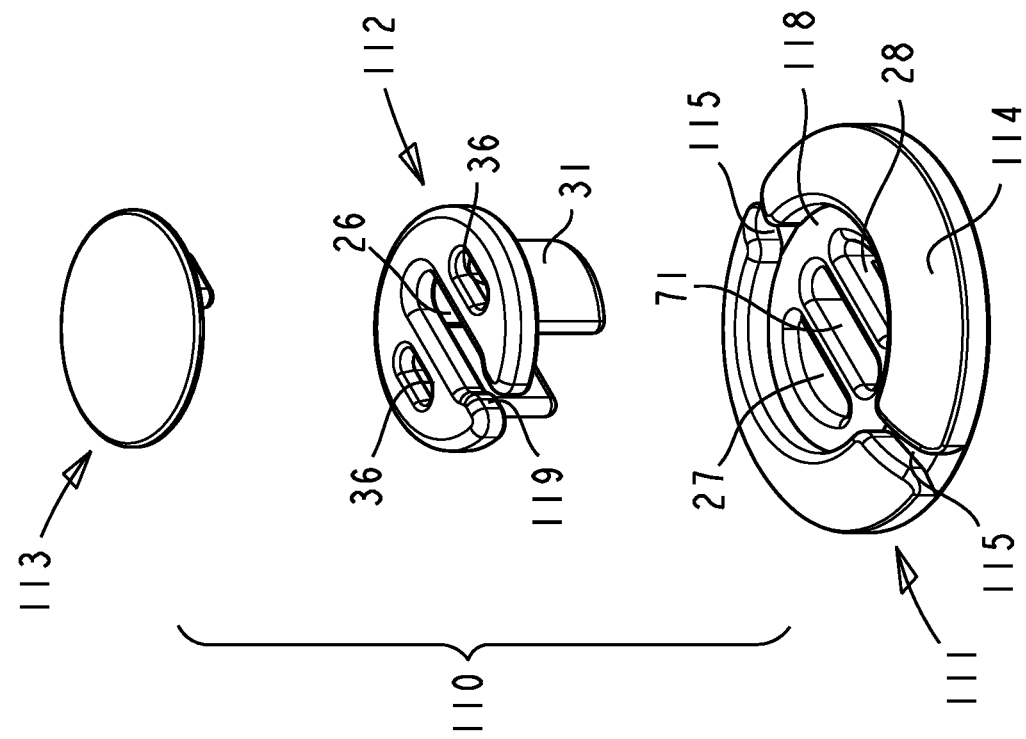
Fig. 11A
Fig. 11B

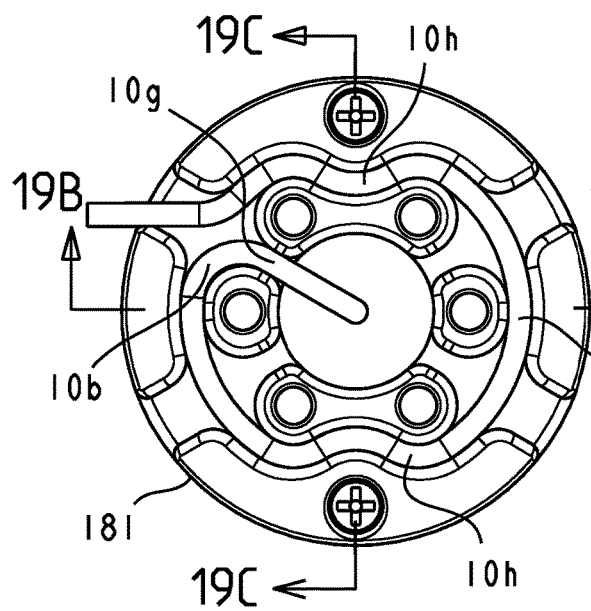
Fig. 18A
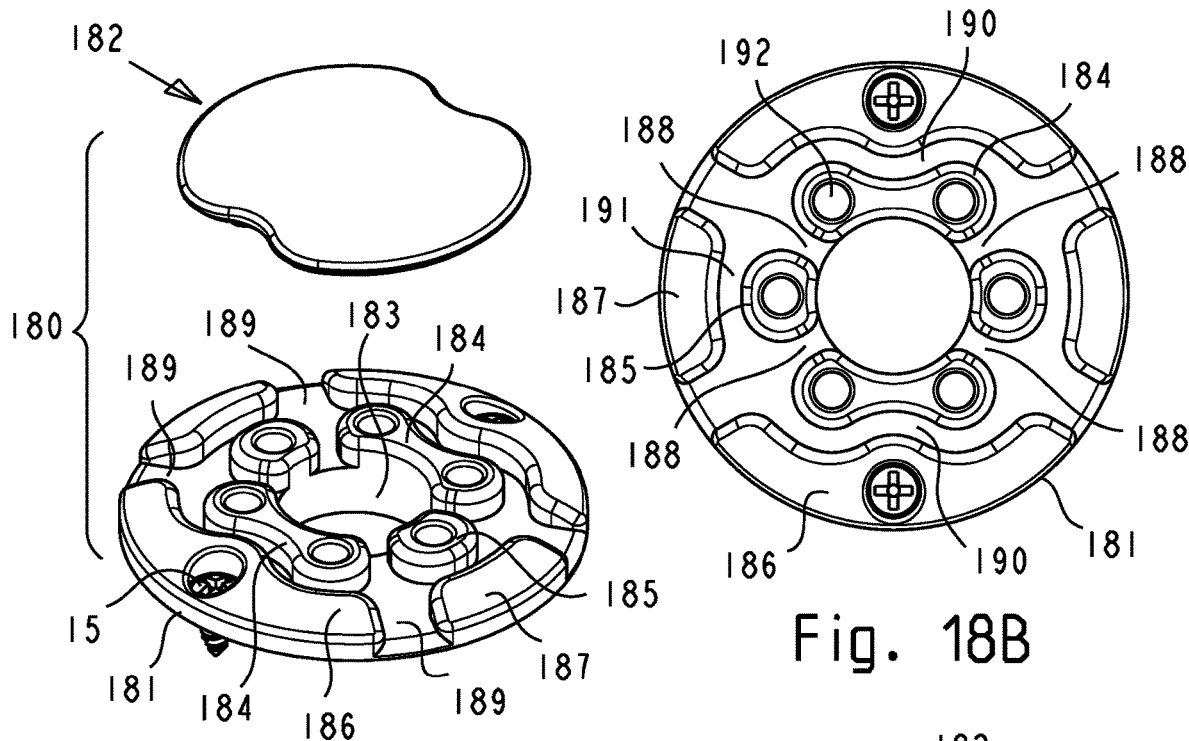
Fig. 18B
Fig. 19B
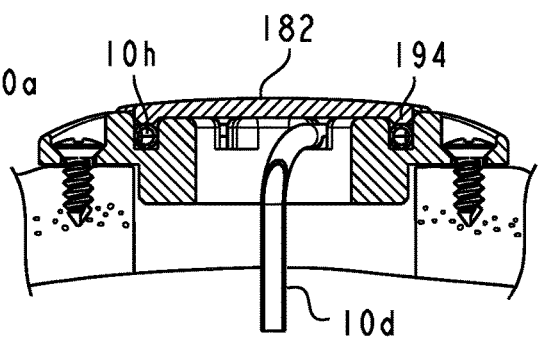
Fig. 19A
Fig. 19C

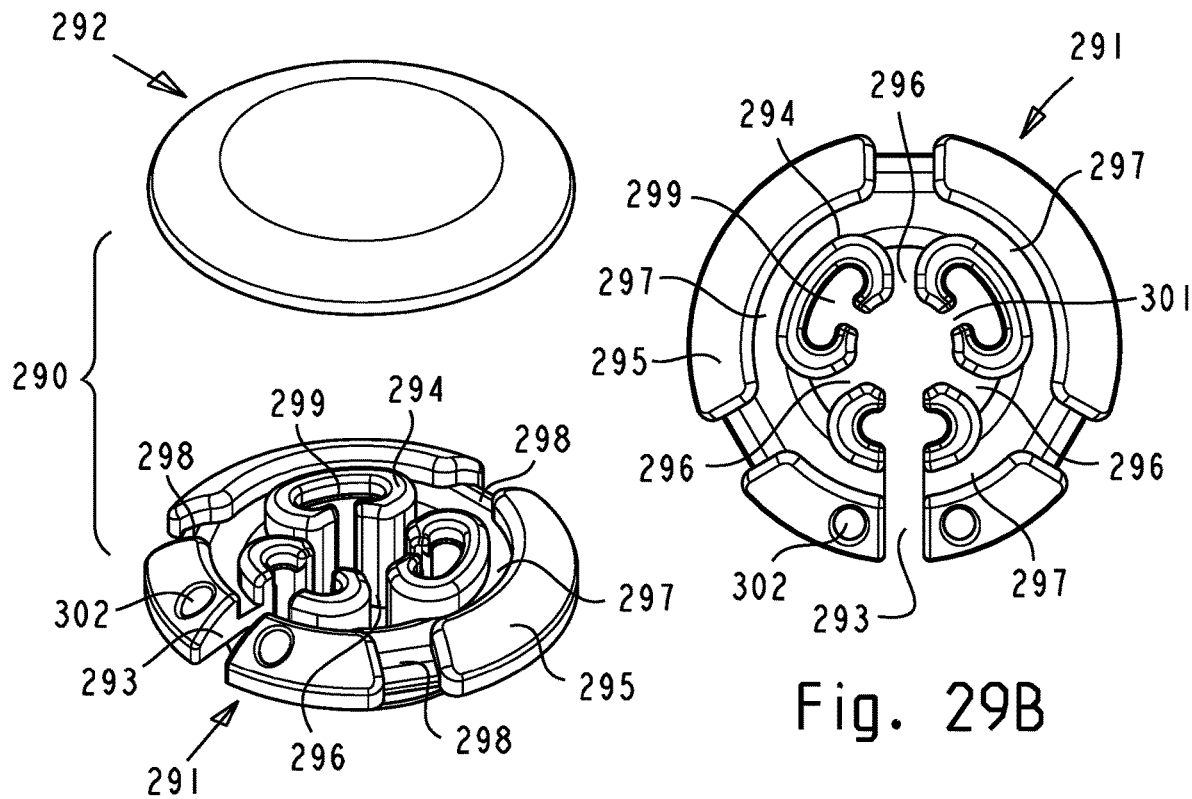
Fig. 29A
Fig. 29B
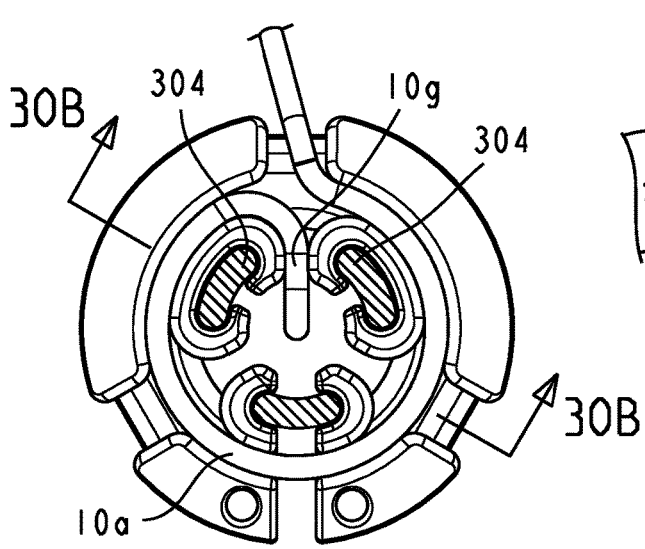
Fig. 30A
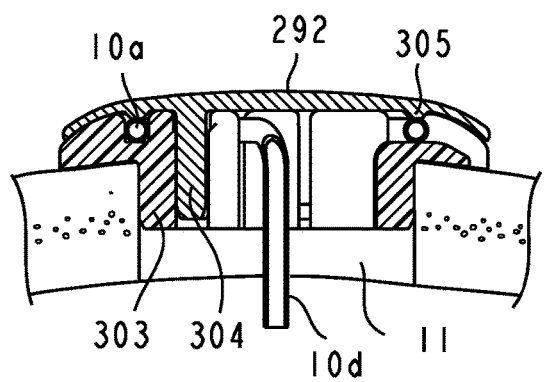
Fig. 30B

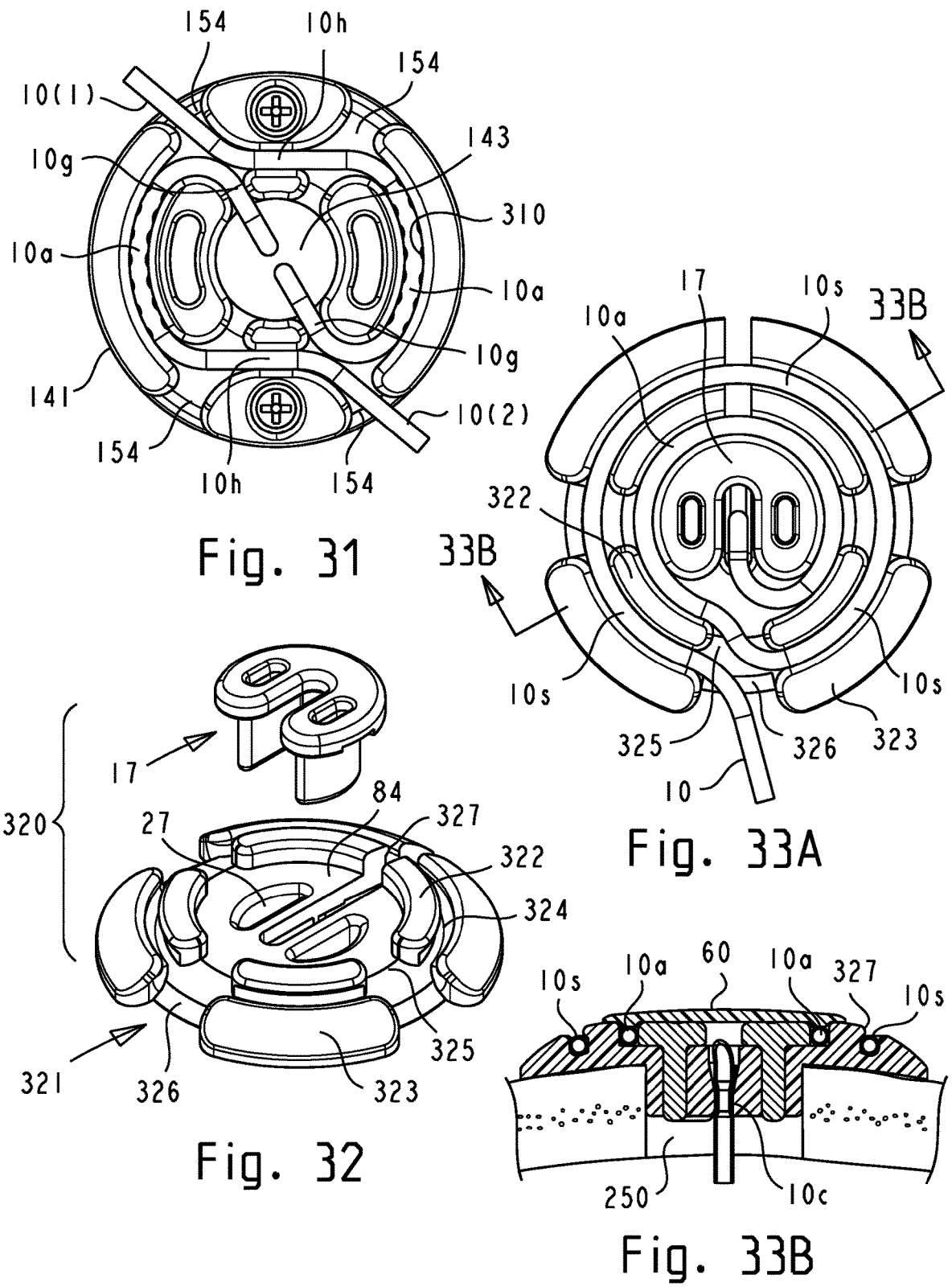

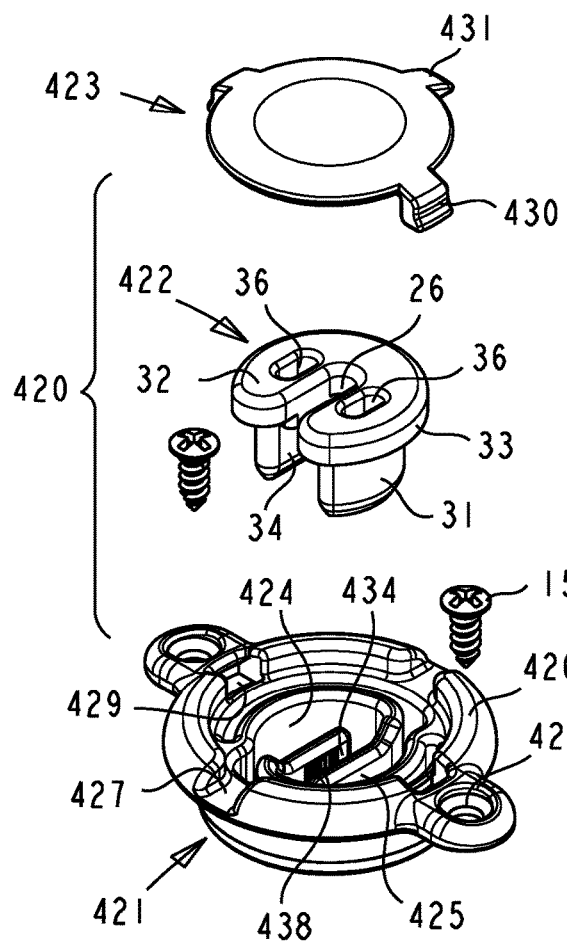
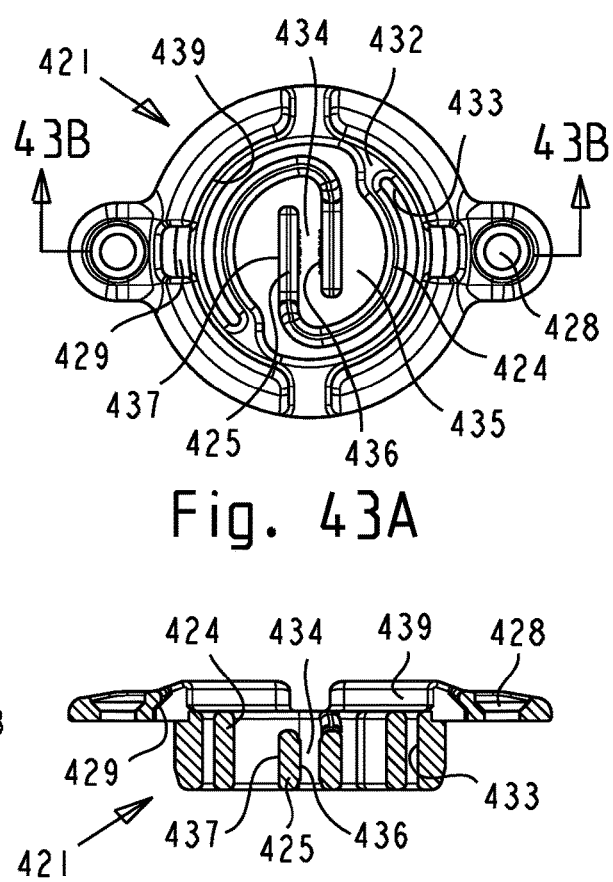
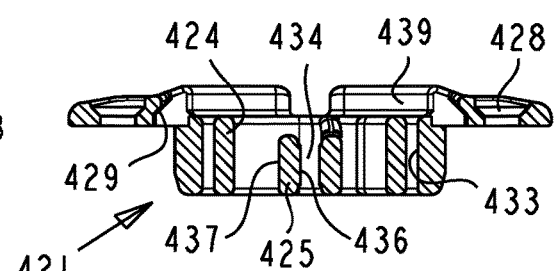
Fig. 43A
Fig. 43B
Fig. 42
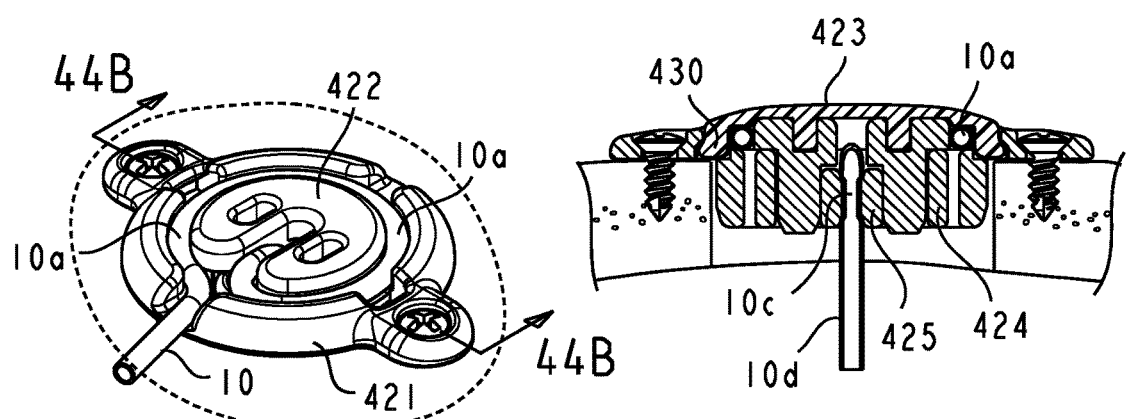
Fig. 44A
Fig. 44B

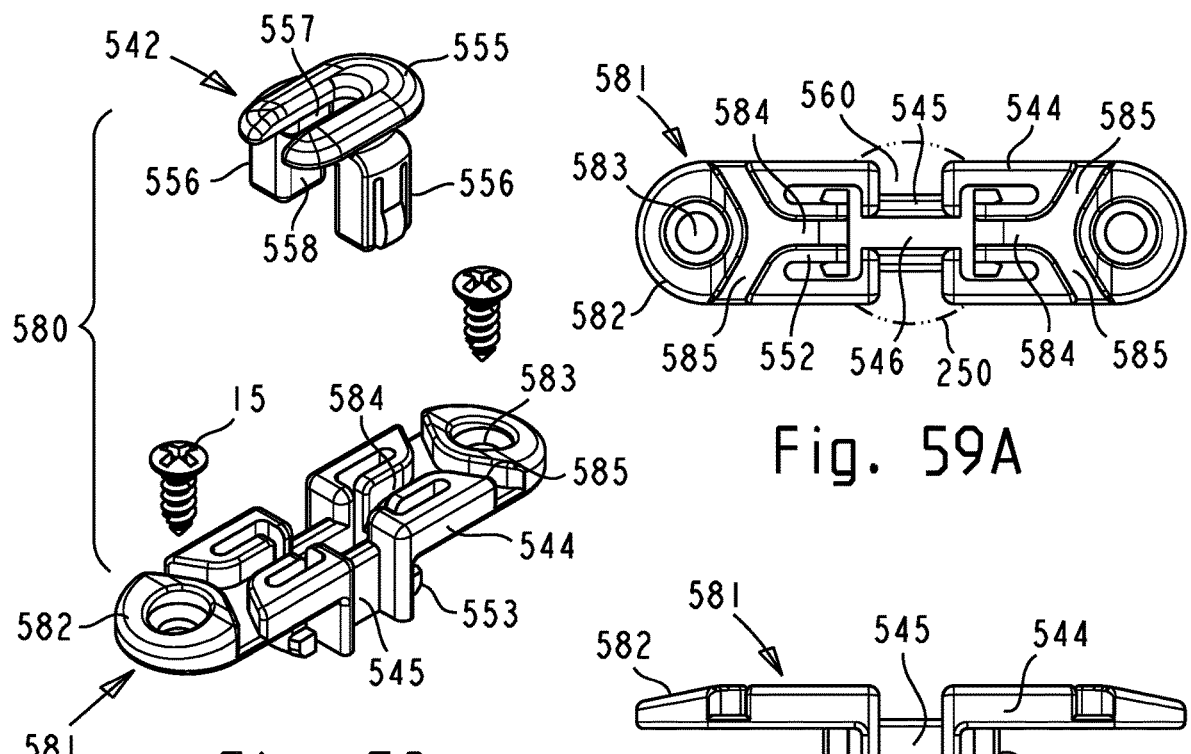
Fig. 58
Fig. 59A
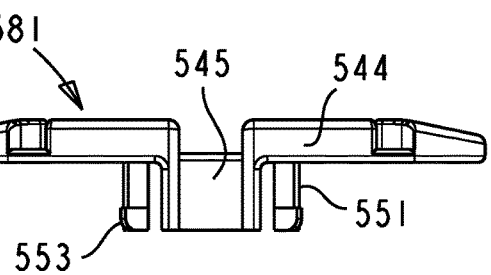
Fig. 59B
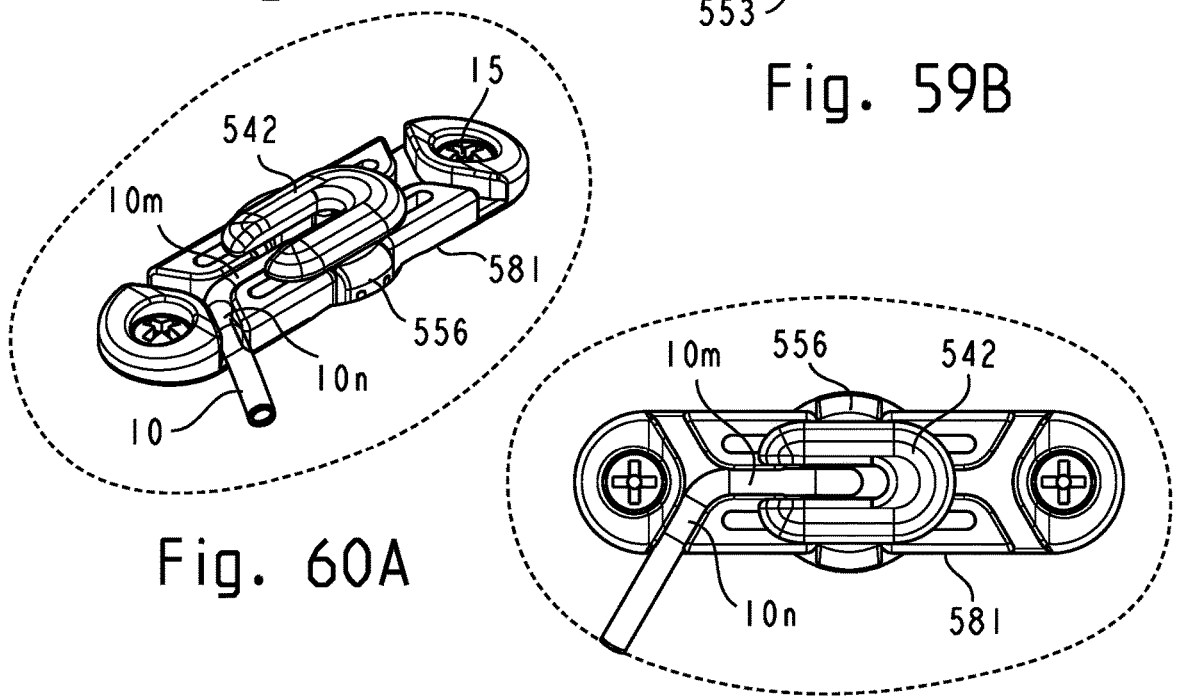
Fig. 60A
Fig. 60B

DBS LEAD FIXATION DEVICES HAVING A CLAMP AND/OR PERIPHERAL LEAD RETENTION GROOVES

BACKGROUND

Prior Art

Deep brain stimulation (DBS) of neural structures is an important therapy for treatment of neurological disorders, such as Parkinson's disease, dystonia, essential tremor, epilepsy, and other debilitating conditions. The therapies are delivered through electrical leads which transmit electrical stimuli from an implanted device, such as a neurostimulator, to a target neural structure in the brain.

Commonly implanted DBS leads have four or more ring shaped electrodes at the distal end which are connected by thin conductors to respective contacts of a connector terminal at the proximal end. The proximal connector terminal may be connected to an active device implanted in a cranium, or to an extension lead that connects subcutaneously to a device implanted elsewhere in the body.

The distal electrodes of the lead must be precisely implanted in the brain to achieve a desired therapeutic effect. A stereotactic instrumentation, which may include a rigid frame having markers defining a three-dimensional coordinate system, is commonly used in combination with radiographic imaging and/or intraoperative electrophysiological mapping with microelectrode(s), to attain and confirm precise localization of the lead in the specific region of the brain.

The lead is introduced into the brain through a burr hole formed in the cranium of a patient, guided by a cannula precisely positioned by the stereotactic instrumentation. The cannula guides the lead along a predetermined lead insertion trajectory which passes through, or is adjacent to, the anatomical structure in the brain targeted for the therapy. After the lead electrodes are successfully localized in the brain, the lead is typically secured at the burr hole using a lead fixation device (also known as a "burr hole cover", "burr hole plug", or "burr hole device"). It is critically important, that the removal of the lead introduction tools and the activation of the lead fixation device does not dislodge the lead from the target location.

Once activated, the lead fixation device must assure that the distal end of the lead, comprising the electrodes, is securely immobilized and maintained in the target tissue during the rest of the implantation procedure (e.g., when tunneling the lead under the scalp), and while chronically implanted. Some anatomical targets, e.g., subthalamic nucleus, are very small, and even a sub-millimeter dislodgement of the electrodes from the optimal localization may affect the efficacy of the therapy or cause undesirable side effects.

Current DBS lead fixation devices and methods of using them are disclosed in U.S. Pat. No. 9,043,000 to Lane et al (May 26, 2015), U.S. Pat. No. 9,474,896 to Lopez (Oct. 25, 2016), and U.S. Pat. No. 10,517,732 to Paspa et al (Dec. 31, 2019), which are incorporated here by reference. Lane at al discloses a burr hole plug which comprises a plug base, a retainer having a slidable clamping mechanism, and a cover. The retainer comprises a retainer support, a slot formed in the retainer support for receiving the lead, and a clamping mechanism having a clamping bar and a flange slidably engaged with the retainer support. The clamping bar is actuated with a special tool to secure the lead. Lopez utilizes essentially the same slidable clamping mechanism as Lane et al but recognizes the risk of lead dislodgment from the clamp and aims to provide a strain relief by routing the lead, which exited the plug base, back into the plug base, and then again out of the plug base via another exit groove.

Paspa et al discloses a burr hole cover which comprises a retainer and a cap with a gasket. The lead is aligned with one of the channels in the retainer and clamped with a cap pressed into a central opening in the retainer so that the gasket forces the lead against the inside wall of the retainer. The lead may be further retained by pressing it into an exit groove in the retainer. The clamping of the lead in the retainer requires the lead to be manually displaced laterally toward the side wall of the retainer opening before the cap is pressed into the opening. Furthermore, the lead must be manually held against the retainer when the cap is being pushed down into the retainer to prevent the lead from being dragged down with the plug, which could cause dislocation of the lead electrodes at the distal end of the lead.

Generally, in currently used lead fixation devices, clamping involves a small portion(s) of the lead and creates pinch points and abrupt lead transition at the lead exit from the clamp. Excessive localized clamping can damage the lead, while inadequate clamping may allow the lead to slip within the clamp when the lead is pulled away from the device. In the devices where clamping of the lead generates a drag or traction on the lead, unintended dislocation of the lead may occur. Most devices also lack an effective strain relief to absorb an inadvertent external tensile force on the lead, which increases the possibility of dislocation of the lead electrodes from the efficacious localization in the brain.

Majority of currently used lead fixation devices are applicable to a commonly used 14 mm diameter burr hole. These devices have often an intricate clamping mechanism that is not easily scalable for use with smaller burr holes. Smaller burr holes and drill holes (e.g., about 8 mm diameter) have certain advantages that could be realized when smaller devices with a robust clamping mechanism are available.

Thus, there is a need for lead fixation device which would further improve lead fixation, prevent lead damage due to clamping of the lead, provide an effective strain relief within the device, and minimize the risk of lead dislodgement due to removal of the lead introduction tools and activation of the lead fixation device.

SUMMARY

The disclosed lead fixations devices (each referred to hereinafter as the "device") address the need for improved fixation and strain relief of DBS leads at the burr hole. Some devices utilize a clamp having clamping walls activated by a plunger, which imposes a predetermined displacement to the clamping walls. Other devices utilize a system of radial lead retention grooves ("radial grooves") and peripheral lead retention grooves ("peripheral grooves") to securely accommodate a substantial segment of the lead within the device. Still other devices utilize both the clamp and the peripheral lead retention grooves, which provide a dual fixation and strain relief of the lead.

One disclosed device utilizes a clamp comprising clamping walls and an actuating plunger. The plunger is not in a direct contact with the lead. Instead, the plunger imposes the clamping action through interposed clamping walls, which does not create a drag on the lead. Therefore, the action of the plunger does not cause dislocation of the lead.

In one embodiment, a centrally disposed clamp has two opposing clamping walls having actuation surfaces accessible through apertures adjoining the clamping walls. The clamping walls may be an integral part of the device base, or part of an interposer, a discrete part seated in the central opening of the device base. The clamp is activated by pressing actuating tabs of the plunger into the apertures to displace the clamping walls against the lead positioned in a slot between the clamping walls.

The clamp can be activated after the lead is successfully localized in the target and the cannula is retracted from the brain. Alternatively, the clamp can be preactivated against the cannula so that when the cannula is retracted, the clamping action is transferred to the lead. No special tools are required to activate the clamp.

The clamping walls can be configured in the device as normally open, so that the cannula can be inserted between clamping surfaces unimpeded, without being deflected out of the lead insertion trajectory. Alternatively, the clamping walls can be configured as normally closed. In these embodiments, the clamping walls can be spread apart with a removable insert to allow unimpeded access for the cannula. Once the lead is localized, the clamp is activated by removal of the insert.

In another embodiment, the clamp comprises an interposer having a single off-center clamping wall with an actuation surface accessible through a centrally disposed aperture. The clamp is activated by pressing a pin-like plunger into the interposer aperture, wherein the plunger displaces the clamping wall to clamp the lead against the inside wall of the base opening.

Another disclosed device utilizes radial and peripheral lead retention grooves configured to securely retain a substantial segment of the lead by an interference fit. Embodiments of this device can have a rigid or resilient base, with a variety of retention groove configurations. The retention is distributed over a relatively long segment of the lead thus avoiding overstressing the lead. This is in contrast to a localized clamping which can cause pinch points and abrupt bends that can damage the lead. The peripheral grooves communicate with multiple lead exit grooves which enable the lead to exit the device in the desired direction.

Another disclosed device utilizes both a clamp and peripheral lead retention grooves, thus providing a dual fixation of the lead within the device. The two fixation method are synergistic in that the clamp keeps the lead retained when the lead is being pressed into the peripheral grooves, and the retention of the lead in the peripheral grooves provides strain relief for the clamp when an inadvertent external pulling tension is applied to the dually fixated lead.

The disclosed devices provide additional advantageous features. A simple clamp is space efficient and can be activated without special tools. Some embodiments can be adapted for use with drill holes or burr holes much smaller in diameter than commonly used 14 mm, e.g., about 8.0 mm. Other embodiments may have a device base retained in a burr hole by an interference fit generated by installation of the plunger, which compresses the outer walls of the base against the inside wall of the burr hole. Still other embodiments can have a small overall size and/or low profile to minimize scalp erosion and to optimize aesthetic outcome.

Devices with radial and peripheral lead retention grooves can be used to independently secure two leads implanted through a single burr hole, wherein one lead can be secured at the device before the other lead is introduced. In some embodiments, the peripheral retention grooves can be adapted to accommodate multiple lead loops, either side-by-side, or one on top of another. Some device embodiments may enhance sealing of the device from cerebrospinal fluid leak by substantially closing the burr hole. Other advantages may be apparent to those skilled in the art from the drawings, description, and claims below.

DRAWINGS

FIG. 2 is an exploded view of the components of the device of FIG. 1.

FIGS. 3A-3B show the base and the interposer of the device of FIG. 1.

FIGS. 4A-4E show a sequence of assembly of the interposer and the plunger in the base.

FIGS. 5A-5B show examples of routing of the lead in peripheral lead retention grooves.

FIGS. 6A-6C show device of FIG. 1 assembled with a cover.

FIGS. 9A-9G show a sequence of assembly and activation of the clamp in the device having a resilient base with integral clamping walls.

FIGS. 11A-13B show another embodiment of a device having a resilient base with integral centrally disposed clamping walls.

FIGS. 18A-19C show a device having a rigid base with radial lead retention grooves and wavy peripheral lead retention grooves.

FIGS. 24A-25B show a device having mounting holes recessed under the lead exit grooves.

FIGS. 29A-30B show a device having a base with peripheral lead retention grooves, which could be inserted into a burr hole after the lead is introduced into the brain.

FIG. 31 illustrates use of device of FIG. 14A to secure two leads implanted through a single burr hole.

FIGS. 32-33B show a device which enables multiple loops of lead segments to be retained in multiple concentric peripheral lead retention grooves.

FIGS. 42-53B show devices having a circular base with integral arcuate beams having clamping walls on free ends.

FIGS. 54A-60B show devices having an elongated base with integral double ended beams having clamping walls at their midsections.

Figure 1A:
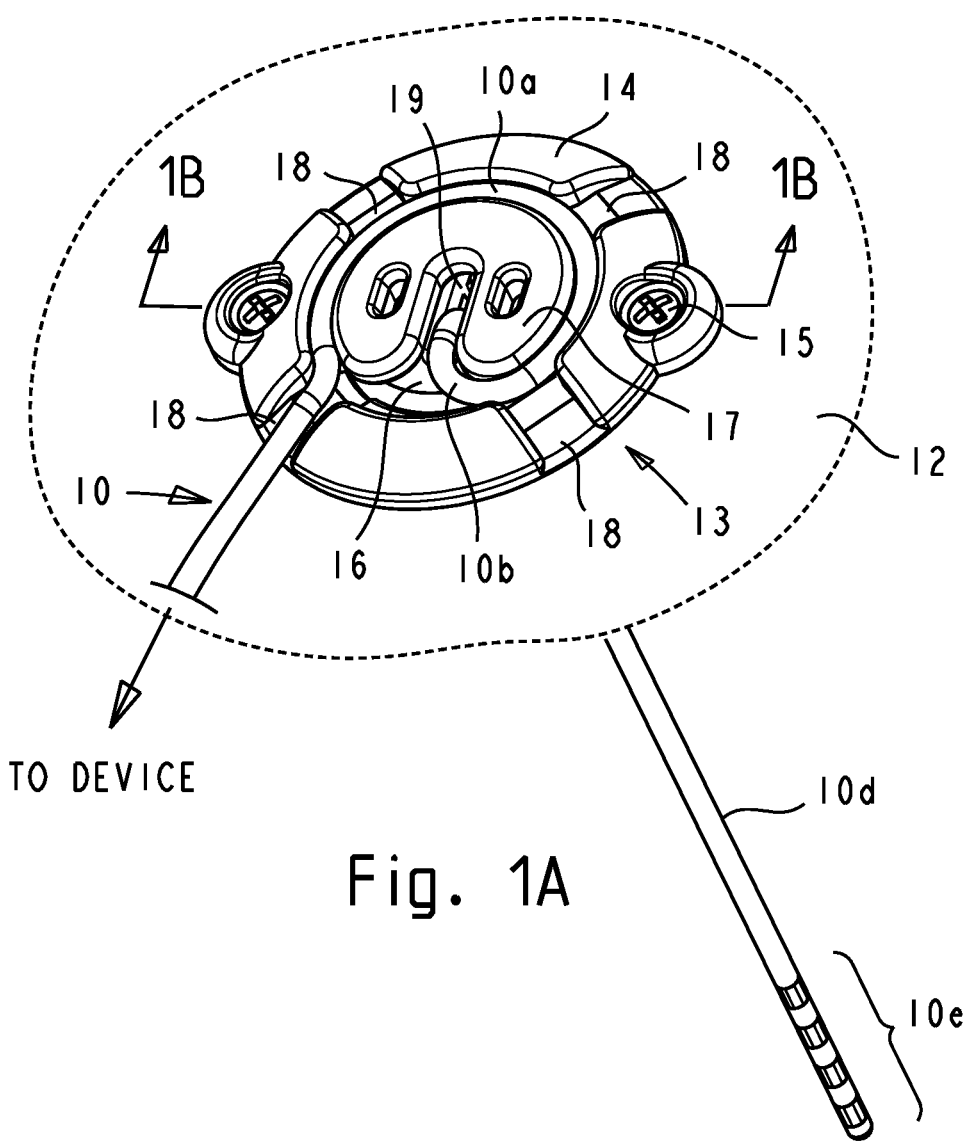
FIGS. 1A-1B show an implanted lead secured at a burr hole by a device with a centrally disposed clamp and peripheral lead retention grooves.

DRAWINGS—REFERENCE NUMERALS 10 medical lead
11 burr hole
12 cranium
13 lead fixation device
14 base
15 screw
16 interposer
17 plunger
18 lead exit groove
19 slot, interposer
20 body, base
21 central opening, base
22 top surface, base
23 ledge, base
24 flange, interposer
25 protrusion, retaining
26 slot, plunger
27 aperture, interposer
28 clamping wall, interposer
29 clamping surface, clamping wall
30 actuation surface, clamping wall
31 actuating tab, plunger
32 top portion, plunger
33 perimeter edge, plunger top portion
34 actuating surface, plunger tab
35 outer surface, plunger tab
36 hole, plunger
37 top inside wall, base opening
38 inside surface, base opening
39 undercut, base
40 target, lead insertion trajectory
41 outer wall, adjoining aperture
42 cannula
43 cannula guide bushing
44 cannula guide holder
45 stylet
46 lower portion, base
47 cut-out, tool access
48 bevel, interposer
49 underside, plunger top portion
50 prying access
60 Cover
61 retention tab, cover
62 peripheral protrusion, cover
70 interposer
71 slot, closed ends, interposer
80 lead fixation device
81 base, resilient
82 flange, base
83 lower portion, base
84 top surface, base
85 top inside wall, base
86 lead exit groove
87 underside, flange
88 undercut, plunger
90 inside wall, burr hole
110 lead fixation device
111 base, resilient
112 plunger
113 cover
114 flange, base
115 lead exit groove
116 underside, flange
117 lower portion, base
118 top surface, base
119 narrowing, actuator slot
140 lead fixation device
141 base
142 cover
143 central opening
144 top surface, base
145 inner protrusion
146 inner protrusion
147 outer protrusion
148 outer protrusion
149 aperture, base
150 mounting hole
151 radial lead retention groove
152 peripheral lead retention groove
153 peripheral lead retention groove
154 lead exit groove
155 retention tab, cover
156 latching feature, cover
157 peripheral protrusion, cover
161 flange, base
162 lower body, base
180 lead fixation device
181 base
182 cover
183 central opening
184 inner protrusion
185 inner protrusion
186 outer protrusion
187 outer protrusion
188 radial retention groove
189 lead exit groove
190 peripheral retention groove
191 peripheral retention groove
192 aperture for cover tabs
193 tabs, cover
194 peripheral protrusion, cover
200 lead fixation device
201 base
203 inner protrusion
204 outer protrusion
205 radial retention slot
206 peripheral groove
207 lead exit groove
208 aperture, base 209 retention tab, cover
210 peripheral protrusion, cover
220 device
221 base assembly
222 tabs, insert molded
223 mounting hole, base
232 tabs, insert molded portion
240 lead fixation device
241 base
242 mounting hole, base
243 top surface
244 base, lower portion
250 burr hole, small
251 burr hole, counterbore
260 lead fixation device
261 base
262 cover assembly
263 cover
264 screw, captive
265 inner protrusion
266 outer protrusion
267 outer protrusion
268 mounting hole
269 threaded hole
271 radial retention groove
272 peripheral retention groove
273 peripheral retention groove
274 lead exit groove
275 peripheral protrusion, cover
281 barb, snap-fit, screw
282 protrusion, cover underside
290 lead fixation device
291 base, resilient
292 cover
293 slit
294 inner protrusion
295 outer protrusion
296 radial retention groove
297 peripheral retention groove
298 lead exit groove
299 aperture
302 hole, base
303 wall, base, lower portion
304 tab, cover
305 cover, peripheral groove
310 rib, peripheral groove
320 device
321 base
322 outer protrusion
323 outer protrusion
324 peripheral retention groove
325 radial passage
326 lead exit groove
327 lip, lead retention
340 device
341 base
342 interposer
343 plunger
344 flange, base
345 lower portion, base
346 central opening
347 side wall, opening
348 slit
349 hole, base
350 interposer, body
351 flange, interposer
352 perimeter, interposer flange 353 aperture, interposer
354 clamping wall
355 outer wall
356 protrusion, snap-in retention
357 cutout, removal access
358 tab, plunger
359 top portion, plunger
360 hole, plunger
380 lead fixation device
381 base
382 top surface
383 top inside wall
384 peripheral retention groove
385 lead exit groove
410 device
411 base, mounting holes
420 device
421 base
422 plunger
423 cover
424 beam, arcuate
425 clamping wall
426 outer protrusion
427 lead exit groove
428 mounting hole
429 cutout, cover lock
430 tab, cover
431 flap, exit groove
432 fixed end, arcuate beam
433 outer wall, base
434 slot, clamp
435 aperture, base
436 clamping surface
437 actuation surface
438 texture or protrusions
439 top inside wall
450 base
451 slit
452 arcuate beam
453 clamping wall
454 fixed end, arcuate beams
455 aperture, base
456 actuation surface
457 inner arcuate surface
458 clamping surface
459 slot
460 base, showing gap "W"
471 insert, spreading
510 device
511 base
512 plunger
513 cover
514 lower portion, base
515 upper portion, base
516 top inner side wall
517 top inside wall, base
518 arcuate beam, upward extension
519 peripheral retention groove
540 device
541 base, elongated
542 plunger
543 end portion, elongated upper body
544 beam, double-ended
545 clamping wall
546 slot, base
547 clamping surface
548 actuation surface 548 seating area, cranium
549 middle beam, base
550 upper portion, middle beam
551 lower portion, middle beam
552 radial lead retention groove
553 protrusion, interference fit
554 planarized surface, cranium
555 top portion, plunger
556 actuating tab
557 slot, plunger
558 actuating surface
559 retention tab, plunger
560 aperture
561 slit, elongated base
580 device
581 base
582 end section, base
583 mounting hole
584 radial retention groove
585 peripheral retention groove

DETAILED DESCRIPTION

In the ensuing description and claims, "lead" primarily refers to a stimulation lead, a sensing lead, or a combination thereof, intended for chronic implantation. In broader sense, "lead" encompasses any elongated implantable device (e.g., a catheter), which is intended for chronic or acute implantation, and can be advantageously secured by the disclosed devices. "Lead introduction" refers to the procedure of implanting the lead, including use of temporary electrode probes for physiological mapping of the target site and test stimulation, required to verify electrode localization and to confirm a desired therapeutic effect. "Trajectory" refers to a straight path through the tissue to the intended target location in the brain, as defined by lead introduction tools. "Target" refers to the ideal or optimal location for the lead electrode(s) implantation, near or within the structure of the brain to be treated. "Proximal" and "distal" use a device or an external instrument as the reference, i.e., "proximal" means proximal to the device and "distal" means distal from the device. Similarly, a proximal direction is the direction toward a device and a distal direction is the direction away from the device and toward the target tissue in the brain. When describing components and features of a device "inward" means toward the center of the device, and "outward" means away from the center of device. "Upper" and "top" is on the exterior side of the device while "lower" and "down" is on the interior side of the device or the burr hole. "Radial groove" refers to a groove substantially aligned with the radial direction, originating from the center of the device and/or burr hole. "Peripheral groove" refers to a grove that has a direction that is normal to, or substantially departing from, the radial direction.

Figure 1B:
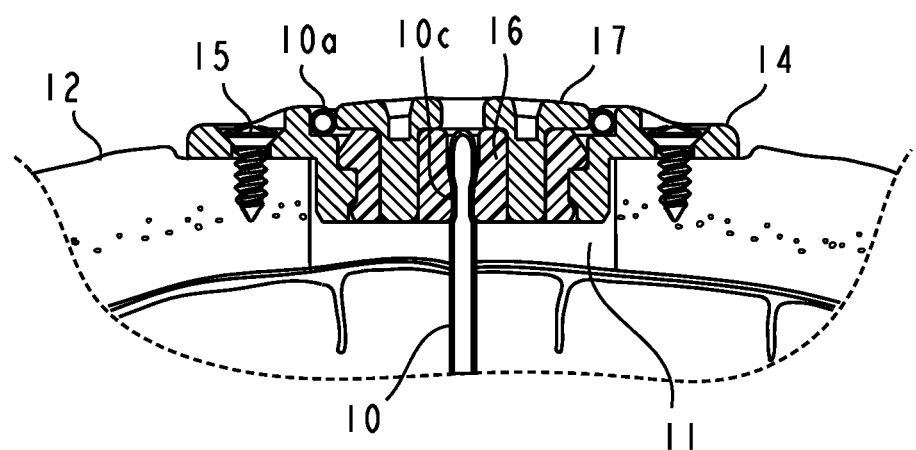

FIGS. 1A-1B provides an overview of a device embodiment with a centrally disposed clamp and peripheral lead retention grooves, with more detailed description following thereafter. A DBS lead 10 is implanted in the brain through a burr hole 11 in a cranium 12. The distal end of the lead 10d, comprises electrode terminal 10e, which is localized in the predetermined target tissue of the brain, where a successful therapy can be delivered. The lead is secured at the burr hole by a lead fixation device 13.

Device 13 comprises a base 14, which is affixed to the cranium with bone screws 15. A clamp assembly comprising an interposer 16 and a plunger 17 is installed and activated in the central aperture of base 14 to clamp the lead segment 10c. The lead is clamped in the centrally disposed slot 19, and the portion of the lead exiting the slot is transitioned at the segment 10b into the peripheral lead retention grooves formed between the top perimeter of plunger 17 and the opposing top inside wall of the base. Lead segment 10a are pressed into the peripheral grooves to provide further retention and strain relief.

Lead segment 10b may be transitioned into the peripheral grooves in a clockwise or in a counterclockwise direction to a preferred lead exit groove in the base. After the lead is fully secured at the device, it can be tunneled under the scalp toward an implantable active device which will deliver the therapy.

FIG. 2 shows the component parts of device 13 in an exploded view. Base 14 comprises a body 20, which may be ring-shaped, with a central opening 21 providing passageway for the lead and configured to receive interposer 16 and plunger 17. The opening comprises a top surface 22 for seating the lead, and a ledge 23 for seating the interposer. The base further comprises radial grooves 18 for lead exit from the device.

Interposer 16 comprises a flange 24 for seating the interposer on ledge 23 of the base, and protrusions 25 for snap-fit retention of the interposer in the base. The interposer further comprises a centrally disposed slot 19 and two apertures 27 symmetrically disposed about the slot. The interposer further comprises two clamping walls 28 adjoining the slot. Each clamping wall has a clamping surface 29 facing the slot, and an actuation surface 30 accessible through a respective aperture 27.

Plunger 17 comprises two actuating tabs 31, attached to a top portion 32. The top portion has a centrally disposed slot 26 and a perimeter edge 33. In this embodiment the slot has an open end and may have a width greater than the diameter of a cannula, to allow the plunger to be positioned directly above the burr hole with the cannula present without interference with the cannula. Each tab comprises an inwardly facing actuating surface 34 and an outer surface 35. The clamping action results when the plunger tabs are pressed into respective interposer apertures 27, causing clamping walls 28 adjoining the slot to be displaced inwardly toward each other. The top portion of the plunger may also have holes 36, which can be used to locate and retain a cover, as shown in FIGS. 6A-6C.

FIG. 3A shows cross sectional details of base 13 and interposer 14. The base opening comprises a top inside wall 37, an inside surface 38, and an undercut 39. When the interposer is seated in the base, the underside of flange 24 rests on ledge 23, and protrusions 25 snap-fit into undercuts 39, thus retaining the interposer in the base. Alternatively, the undercuts 39 may be absent, and protrusions 25 may snap-fit behind the underside of the base body. The outer walls 41 of the interposer may have outside dimensions sized to allow rotation of the interposer in the base prior to activation of the clamp.

If the lead introduction trajectory is not aligned with the center of the base opening, as depicted by the off-center target 40, the interposer can be rotated in the base to align slot 19 with the lead insertion trajectory, as shown in FIG. 3B. The actuator may be partially inserted into the interposer and used as a tool to rotate the interposer. With the interposer partially inserted, the clamp is not yet activated, and the cannula can move freely through slot 19. A side contact between the cannula and the interposer could laterally deflect the cannula and thus introduce an error into the lead insertion trajectory.

After the lead is introduced and cannula is withdrawn, the clamp assembly can be rotated before clamp activation to align it with a desirable lead exit groove 18, since a small lateral movement of the lead will not cause significant longitudinal dislocation of the electrode terminal from the target tissue. When the clamp is activated, outer walls 41 of the interposer may be compressed by outer surfaces 35 of the actuator tabs against the inside surface 38 of the base opening to positively lock the interposer from rotation in the base.

FIGS. 4A-4F illustrate installation of the device at the burr hole. Lead 10 may be implanted with the aid of a stereotactic instrumentation, which maintains a cannula 42 on a predetermined lead insertion trajectory. The cannula may be guided by a guide bushing 43 held by a guide bushing holder 44. The guide bushing holder may be attached to a stereotactic arc or other instrumentation (not shown) that defines the lead introduction trajectory. Lead 10 is introduced into the brain through the cannula with the aid of a stylet 45, which also provides flexural stiffness to the distal end of the lead as it emerges from the cannula.

When the stereotactic instrumentation is in place, a pointed rod may be inserted into a cannula guide to mark the center point for drilling the burr hole. The burr holes are cut with specialized cranial perforators and drill bits with standard diameters ranging from 4 mm to 14 mm. In DBS applications, lead fixation devices are typically used with a 14 mm diameter burr hole, which provides ample opening for surgical access and a robust fixation mechanism. The outside diameter of the lower portion 46 of the base (seen in FIG. 3A) can be sized for a close fit in the burr hole. If the perforator bit follows entry point determined by the lead introduction tools, the lead will generally be centered in the opening of the base. However, a small deviation from the center may be present due to perforation and drilling tolerances and base tolerances. A larger deviation may occur due to an adjustment of the lead introduction trajectory after the hole is drilled.

If the trajectory is off-center relative to the center of the base, rotating the interposer so that the off-center bias is toward the closed end of slot 19 will result in the optimal orientation of the interposer, which will eliminate any lateral displacement of the lead and allow more room for transitioning the lead into the retention groove. In this orientation the cannula will move without interference with the clamping walls. A cannula or a pointing rod, guided by the guide bushing can be used as target 40 reference, to rotate the interposer so that slot 19 aligns with the lead insertion trajectory, as illustrated by the off-center trajectory location 40 in FIG. 3B.

Base 14 can be attached to cranium 12 with bone screws 15, preferably before implantation of the lead into the brain. The open-ended interposed slot 19 allows seating of the interposer in the base either before or after the lead is introduced. If the open end of slot 19 is oriented in the first direction as indicated by the arrow A, the open end of slot 26 in the plunger should preferably be oriented in the second direction, as indicated by the arrow B. If the lead insertion trajectory is substantially centered in the burr hole, the interposer can be rotated relative to the base to align the closed end of slot 19 with any desirable lead exit groove, as shown in FIG. 4C. The rotation can be accomplished without using a special tool. The plunger, with actuation tabs partially inserted into the interposer apertures, as shown in FIGS. 4C and 4D, can be used to rotate the clamp assembly relative to the base.

After the distal end of the lead is localized in the anatomical target in the brain, the cannula is raised as indicated by arrow C in FIG. 4C. Subsequently, the clamp is activated by pressing the actuating tabs of actuator 17 into apertures of the interposer, as shown in FIGS. 4D and 4E. When the stylet is retracted, the clamp may be activated in any angular orientation relative to the base even when the lead is off-center relative to the base. However, if the lead is not centered in the base, a slight lateral displacement of the lead at the exit from the burr hole will occur. Such lateral displacement can be avoided by seating the interposer in the optimal orientation (with slot 19 aligned to the off-center lead) and selecting alternate lead exit groove 18 which is angularly offset from slot 26.

The device includes clamp deactivation features to allow removal and/or replacement of the lead without detaching the base from the cranium; the base has cutouts 47 adjoining lead exit grooves 18, and the interposer has a bevel 48 on flange 24. When device is assembled as shown in FIG. 4E, the cutouts and the bevel form a prying access 50 to the underside 49 of the top portion of the plunger, which can be accessed by a prying tool via lead exit grooves.

FIGS. 5A-5B show lead 10a retained in the retention groove formed by perimeter edge 33 of the top portion of the plunger and top inside wall 37 of the base opening. Top surface 22 of the base forms the bottom of the groove. The width of the groove is smaller than the outside diameter of the lead, sized to create an interference fit retention of the lead sufficient to prevent release of lead segments 10a when an inadvertent external tension is applied to the proximal portion of the lead.

FIGS. 5A-5B further illustrate how the same exit 18 can be taken from different angular orientations of the clamp assembly with respect to the base. If desired, other exits can be taken. The transition 10b can be directed clockwise or counterclockwise to maximize the length of segment 10a of the lead retained in the peripheral groove. In any case, a lead exit groove that will maximize the length of lead segments 10a retained in the retention groove will maximize lead retention. The relatively long retention length and the curvature of the retention groove enables an effective retention of the lead at a moderate interference fit. A texture or protrusions can be added to the surfaces forming the groove to increase friction and thus to further increase lead retention.

FIGS. 6A-6C show device 13 further comprising a cover 60. The cover has retention tabs 61 for locating and retaining the cover in holes 36 of the plunger. The cover further has a peripheral protrusion 62 that follows the outline of the peripheral lead retention groove and maintains lead segments 10a fully inserted into the groove. If it becomes necessary to remove the cover, it can be pried out by accessing the underside 63 of the cover at access space 64, at unused lead exit grooves.

Figure 7A:
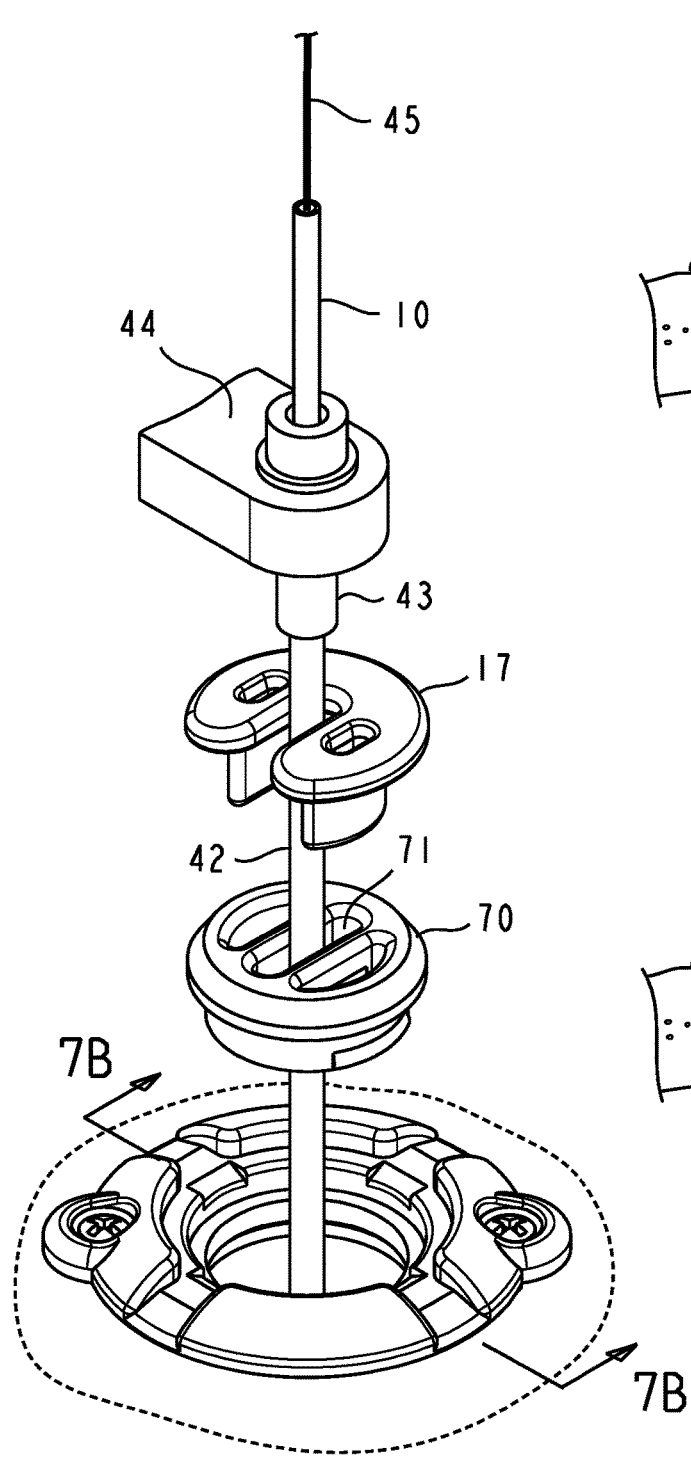
FIGS. 7A-7C show variation of the device of FIG. 1 and an alternate sequence of assembly and activation of the clamp.
Figure 7B:
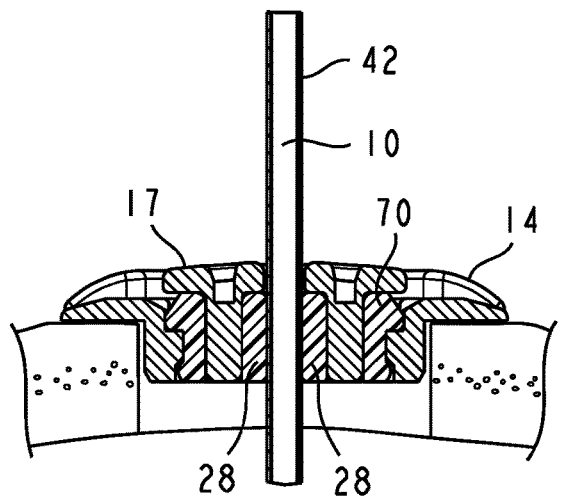
Figure 7C:
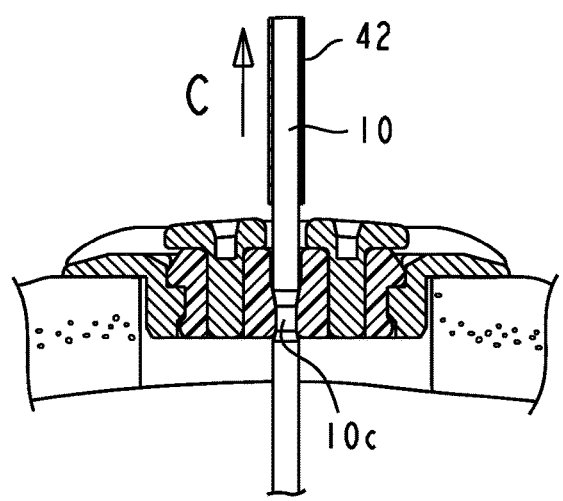

FIGS. 7A-7C show an alternate method of activating the clamp. The clamp is activated with cannula 42 present, as shown in FIG. 7B. The displaced clamping walls 28 of the interposer exert clamping pressure on the cannula. Once the cannula is raised, the clamping pressure is transferred from the cannula to the lead, as shown in FIG. 7C. In this embodiment, an interposer 70 has slot 71 with closed ends, and therefore must be placed on a cannula prior to introduction of the cannula into the brain. This contrasts with interposer 16, which has an open-ended slot and may be inserted before or after the cannula is introduced into the brain. The width of slot 71 may be slightly smaller than the outside diameter of the cannula, so that the interposer could be held in elevated position on the cannula until it is time to seat the interposer in the base.

FIGS. 8A-10C show a device having a base with integrated interposer features. The device can be used with smaller burr holes (e.g., 10 mm or less) and can be mounted at the burr hole without fasteners after the lead is implanted. Having the burr hole uncovered during implantation of the lead is especially advantageous when small burr holes are used. Further advantage is fewer components due to elimination of a discrete interposer and mounting screws.

Figure 8B:
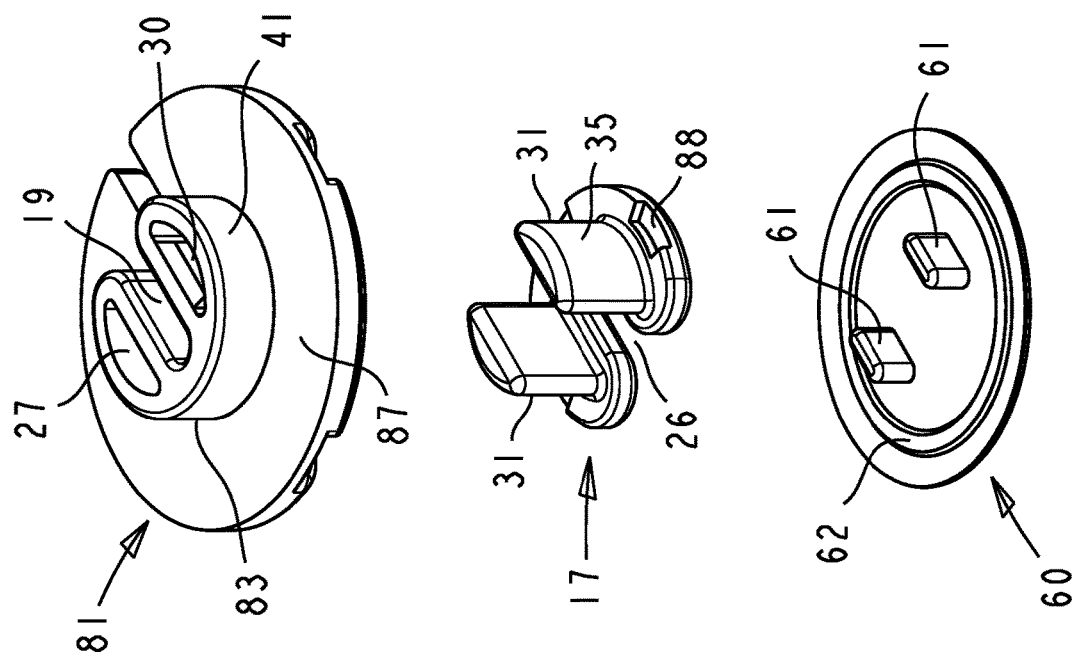
FIGS. 8A-8B show components of a device having a resilient base with integral centrally disposed clamping walls.
Figure 8A:
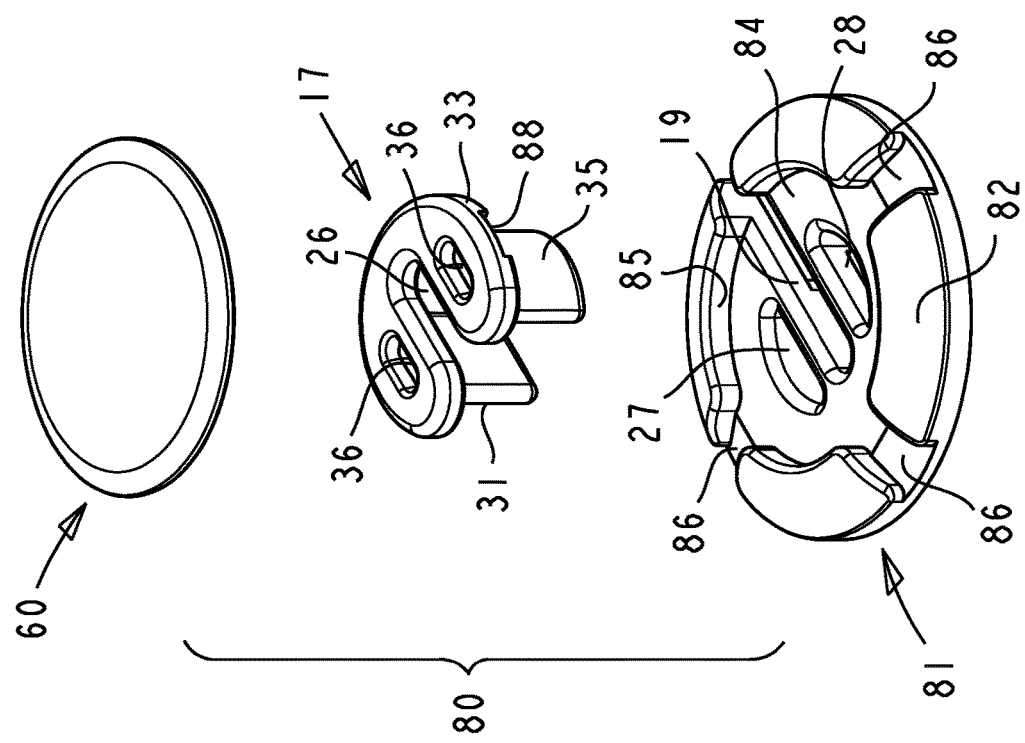

Referring to FIGS. 8A-8B, a device 80 comprises a resilient base 81, a plunger 17, and a cover 60. The features and functionality of the clamp in device 80 are substantially the same as in device 13 described above. However, slot 19, apertures 27, clamping walls 28, and other interposer features are integrated with the base. The plunger and the cover can be essentially the same as in device 13.

Base 81 has a flange 82 for seating the base on a cranial surface, and a lower portion 83 configured to be retained in the burr hole, as explained below. The base further has a top surface 84 and a top inside wall 85 adjoining the top surface, and radial lead exit grooves 86 extending from top inside wall outwardly through the flange. The underside 87 of the flange may be profiled to better conform to a cranial surface. Slot 19 is extended through the flange to allow positioning of the base directly above the burr hole with the cannula present.

FIGS. 9A-9G show a sequence of assembly and activation of the clamp in device 80, which is similar to the sequence described above with reference to the clamp of device 13. After the lead is localized in the brain, the clamp is activated by pressing the actuating tabs of plunger 17 into apertures 27 in the base, as shown in FIGS. 9D-9G. The tabs force clamping walls 28 toward each other to clamp a lead segment 10c. At the same time, the tabs compress the outer walls 41 in the lower portion of the base against the inside wall 90 of the burr hole, thus retaining the base in the burr hole.

Figure 9B:
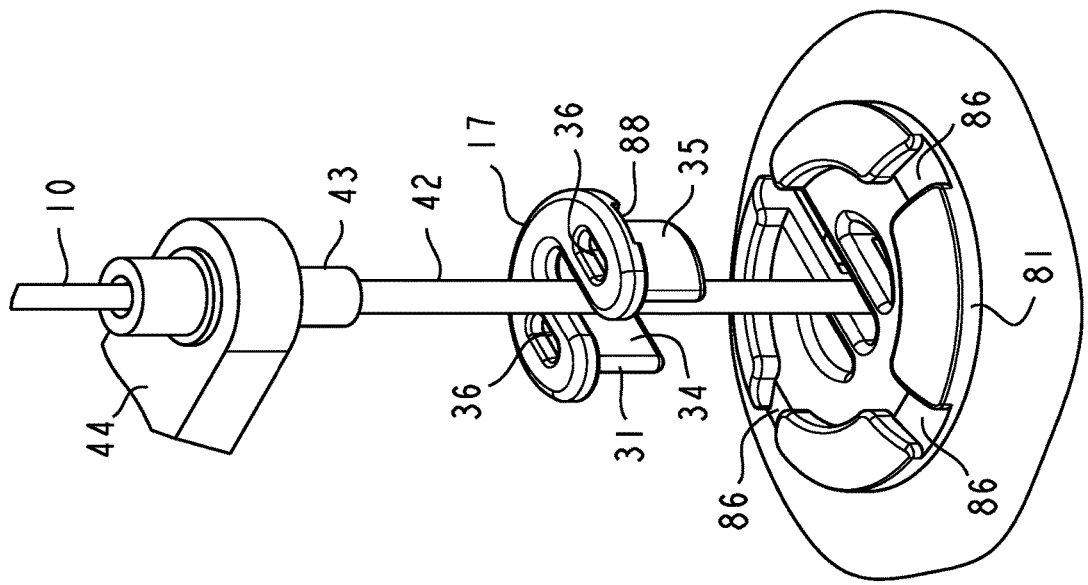
Figure 9A:
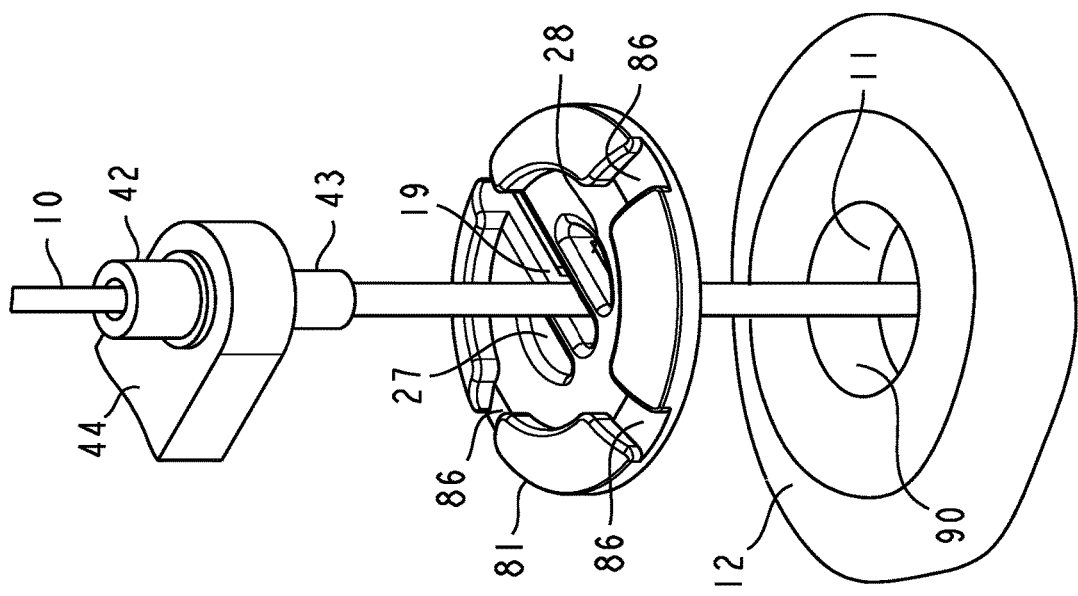
Figure 9F:
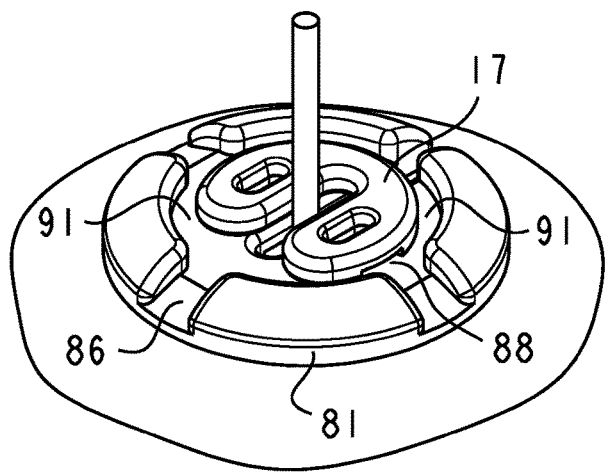
Figure 9G:
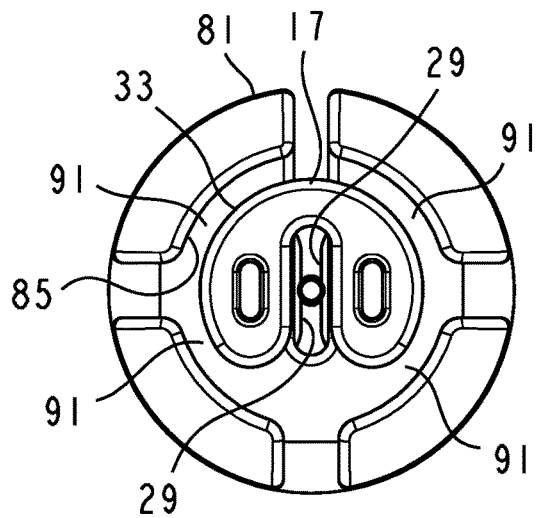
Figure 10A:
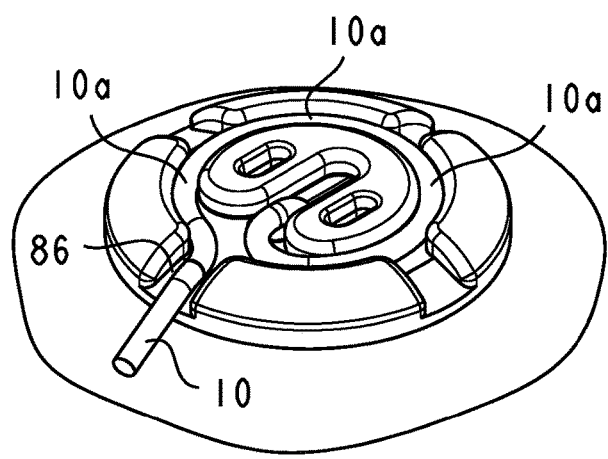
FIGS. 10A-10C show the device with a resilient base having integral clamping walls, with the lead clamped and further retained in peripheral lead retention grooves, and a cover installed.
Figure 10B:
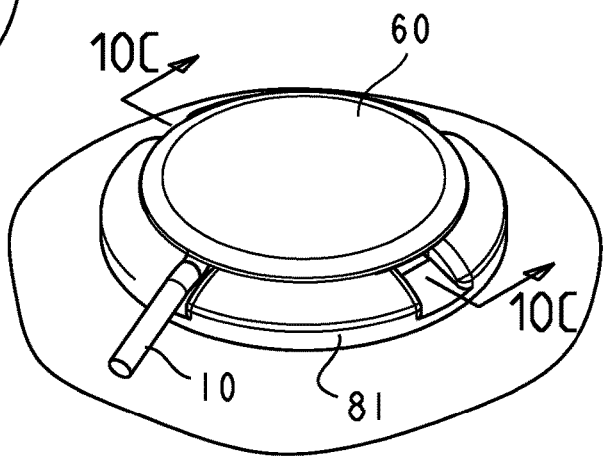
Figure 10C:
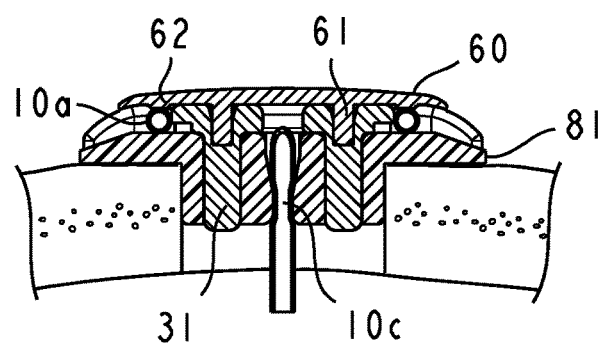

Once the clamp is activated, peripheral lead retention grooves 91 are formed between the perimeter edge 33 of the plunger and the opposing top inside wall 85 of the base, best seen in FIG. 9G. Lead segments 10a are pressed into the peripheral grooves to provide an additional retention mode (in addition to the clamp) and strain relief for the lead. FIGS. 10B-10C show the device with the lead secured in the clamp and in the peripheral retention grooves, with cover 60 installed. If it becomes necessary to deactivate the clamp, segments 10a are removed from the peripheral grooves and the plunger is pried out by accessing undercuts 88 of the plunger at lead exit locations, as indicated by the arrow 88 in FIG. 9E.

FIGS. 11A-13C show a device 110, similar to device 80 described above in that it has a centrally disposed clamp with interposer features integrated with the device base. While device 80 has peripheral lead retention grooves, device 110 has alternate secondary retention features, which makes it possible to make the device smaller in overall dimensions. The device comprises a resilient base 111, a plunger 112, and a cover 113. The base comprises a flange 114 having radial lead exit grooves 115. The underside 116 of the flange may profiled, as shown in FIG. 13B, to better comply with the cranial surface around the perimeter of the burr hole. The base further comprises a lower portion 117 which may be sized for an interference fit in the burr hole. The base comprises two integral clamping walls 28, each having adjoining aperture 27. Slot 71 between the clamping walls has closed ends, similar to the embodiment shown in FIGS. 7A-C. Alternatively, the slot may have an open-end, as in device 80. The base further comprises a top surface 118 and outer walls 41 adjoining the apertures. Plunger 112 comprises a narrowing 119, sized to retentively secure a segment of the lead exiting the clamp.

FIGS. 12A-12D show a sequence of assembly and activation of the clamp in device 110. The base and the plunger may be held in the raised position above the burr hole so that full surgical access to the burr hole is allowed during implantation of the lead. Slot 71 may be narrower than the diameter of the cannula to allow holding the base on the cannula by an interference fit, without additional tools, such as clips. After the lead is localized in the brain, the base may be lowered and pressed into the burr hole.

Figure 12A:
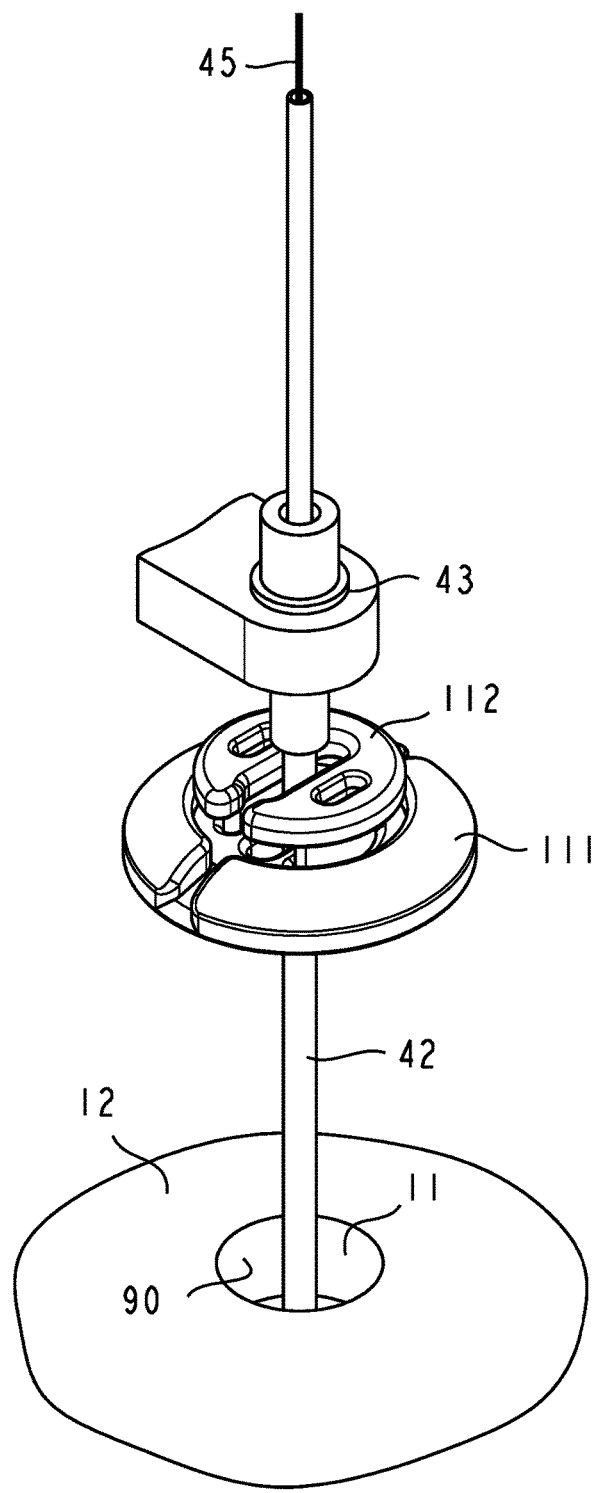
Figure 12B:
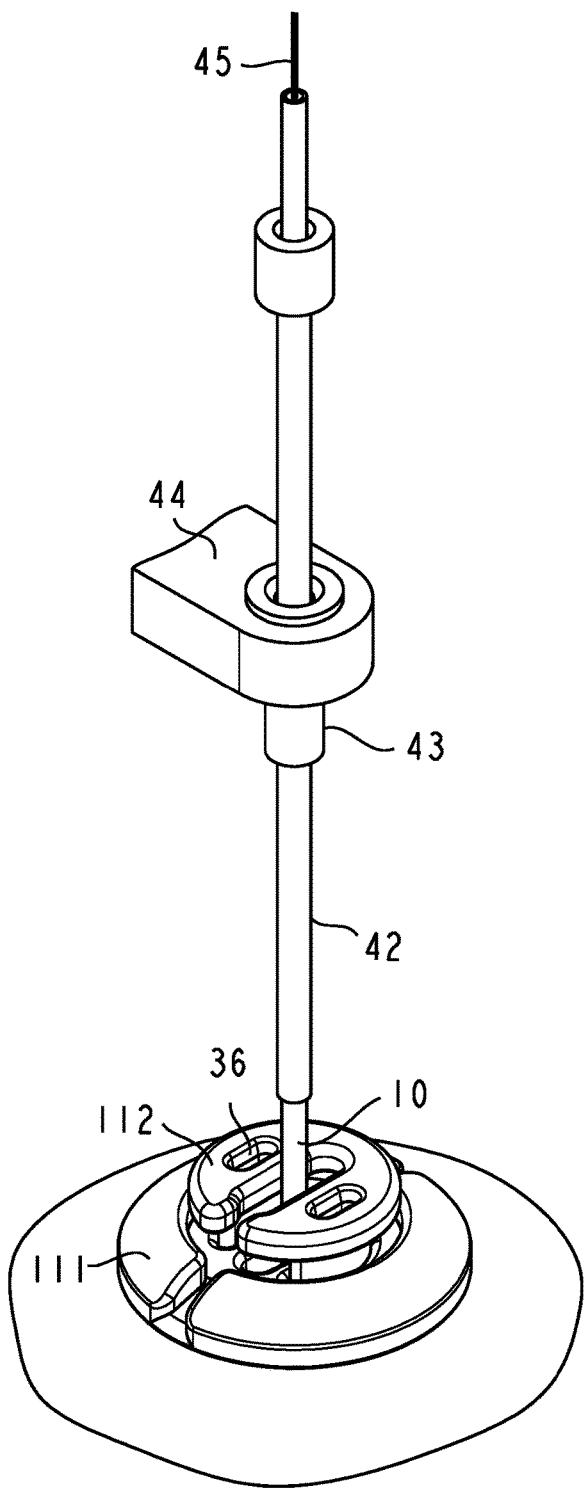
Figure 12C:
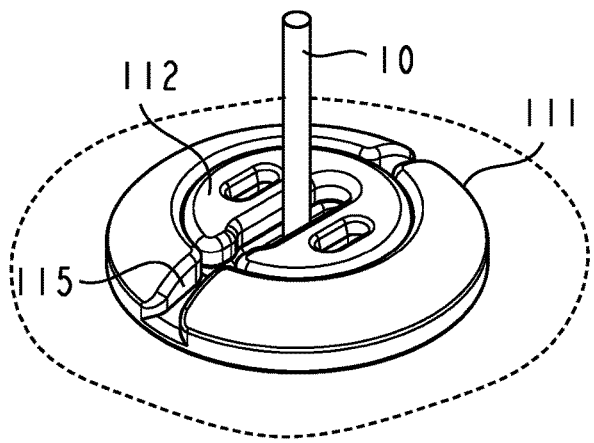
Figure 12D:
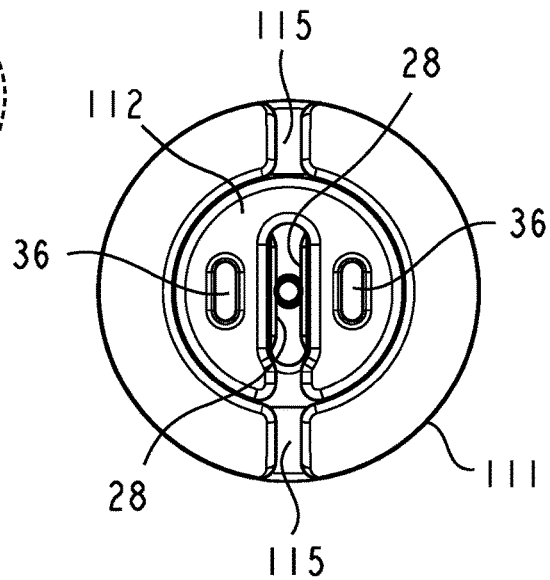
Figure 12E:
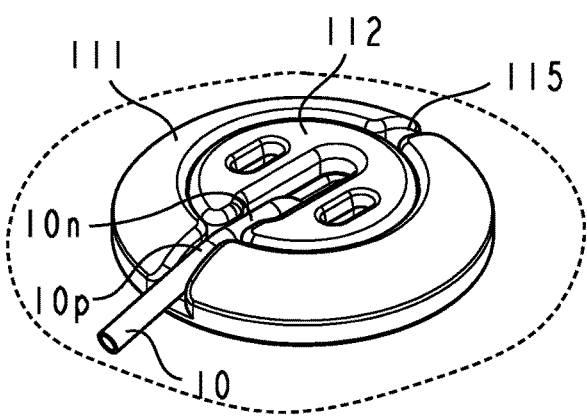
Figure 13A:
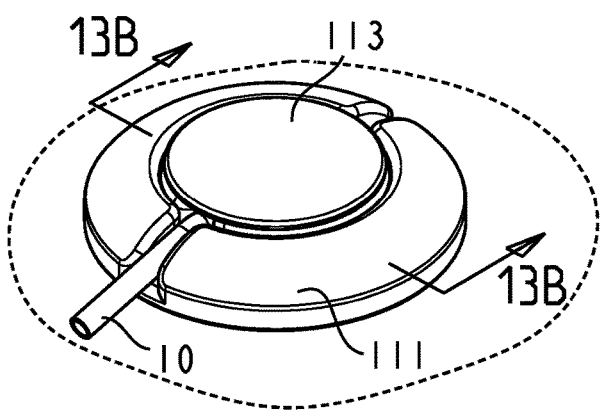
Figure 13B:
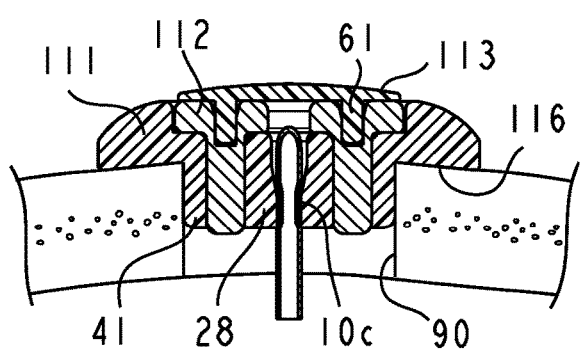

The clamp is activated by pressing the actuating tabs of the plunger into the apertures in the base. The tabs displace clamping walls 28 against lead segment 10c to clamp the lead. The tabs may also compress the outer walls 41 of the base against side wall 90 of the burr hole, thus retaining the lower portion of the base in the burr hole. After the clamp is activated, lead segment 10n is pressed into the narrowing 119 at the open end of the plunger slot, as shown in FIG. 12E. Lead segment 10p may be further pressed into lead exit groove 115 for added retention and strain relief. FIGS. 13A-B show device 110 with the lead secured and cover 113 installed.

Figure 14B:
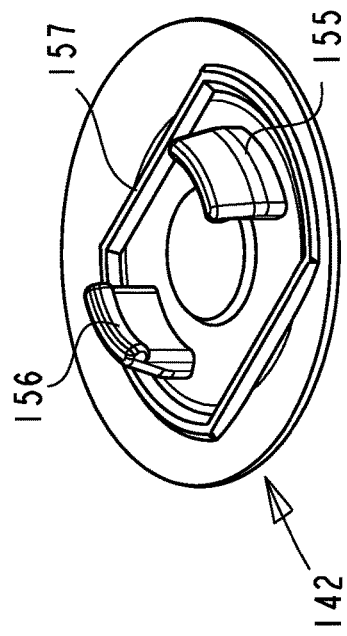
FIGS. 14A-14B show components of a lead fixation device having a base with radial and peripheral lead retention grooves.
Figure 15:
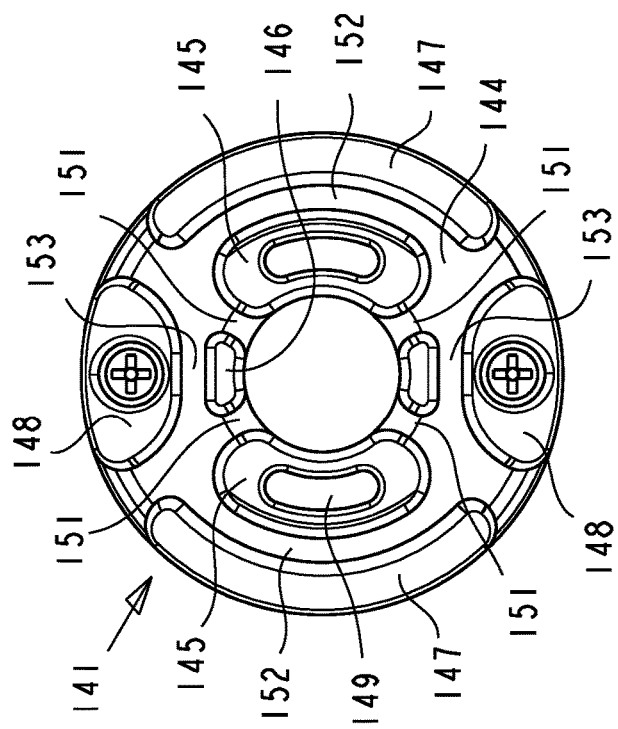
FIG. 15 shows a top view of the base with radial and peripheral lead retention grooves.
Figure 14A:
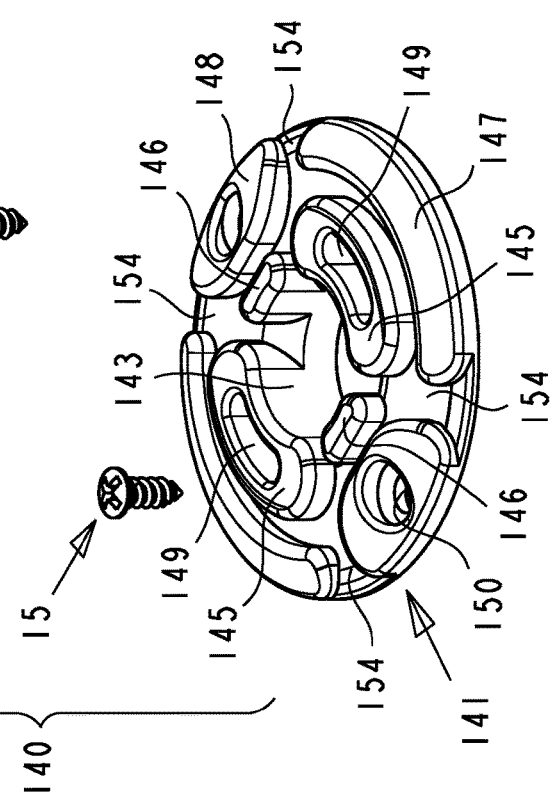

FIGS. 14A-14B show components of a lead fixation device 140, relying on a system of radial and peripheral lead retention grooves to secure a lead at a burr hole. Device 140 comprises a base 141, a cover 142, and screws 15. The base has a central opening 143, which may be circular. On the upper portion, the base comprises a top surface 144, inner protrusions 145 and 146 adjoining the central opening, and outer protrusions 147 and 148, adjoining the outer periphery of the base. Inner protrusions 145 may have apertures 149 for receiving retention tabs extending from the underside of cover 142. Outer protrusions 148 have mounting holes 150 for attaching the base to a cranium with bone screws 15.

In order to receive and retain the lead which extends proximally from central opening 143 and to route the lead to a desirable lead exit from the device, the base comprises a system of grooves formed between opposing side walls of the protrusions. Thus, proceeding from the central opening toward the outer periphery of the base, the base comprises radial lead retention grooves 151 formed between the opposing side walls of inner protrusions 145 and 146, peripheral lead retention groves 152 formed between the opposing side walls of inner protrusions 145 and outer protrusions 147, peripheral lead retention grooves 153 formed between the opposing side walls of inner protrusions 146 and outer protrusions 148, and lead exit grooves 154 formed between the opposing side walls of outer protrusions 147 and 148.

The width of the lead retention grooves may be sized to provide approximately 20% to 30% compression of the lead. For example, for a common 1.27 mm diameter DBS lead having coiled conductors the width of the groove may be about 0.9 mm to 1.0 mm. However, the optimal width will depend on the diameter and construction of the lead, as well as on the length and shape of the grooves and lubricity of materials forming the groove. Different portions of the peripheral grooves may have a different width, configured for a different amount of compression. The side walls forming the groves may have ribs, such as ribs 310 in FIG. 31, or may be textured, to enhance gripping of the lead segments retained in the grooves.

Cover 142 comprises retention tabs 155 which may have a latching feature 156, allowing the tabs to snap in place on the underside of the base, adjacent to apertures 149. The cover further has a peripheral protrusion 157, which follows the outline of the peripheral lead retention grooves 152 and 153 in base 141. The cover may have similar protrusions positioned over the radial lead retention grooves and the lead exit grooves (not shown).

Figure 16A:
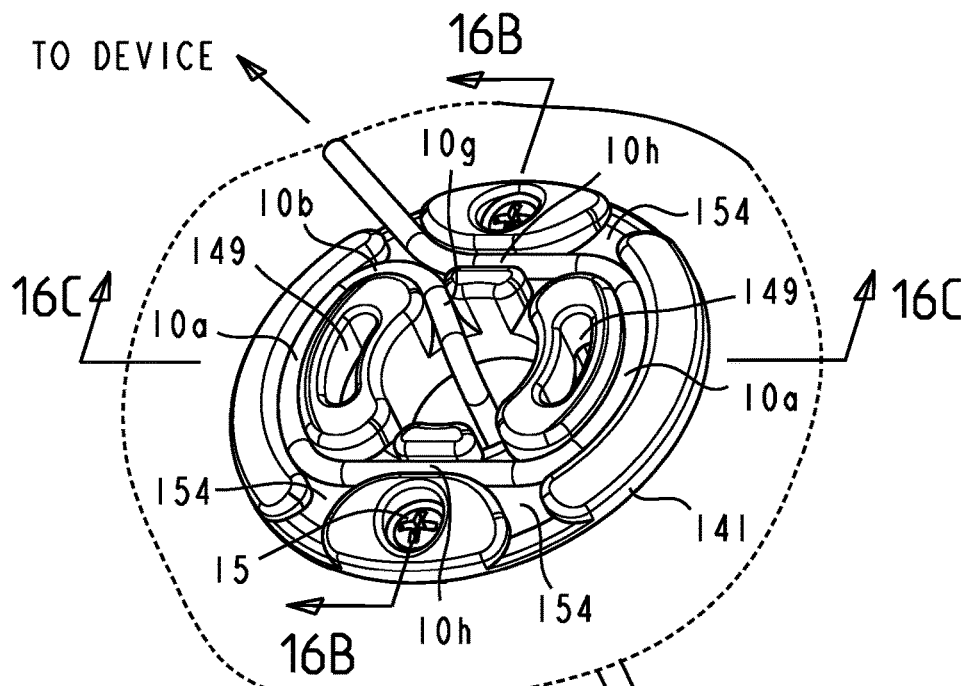
FIGS. 16A-16C show an implanted lead secured by a lead fixation device with radial and peripheral lead retention grooves.
Figure 16B:
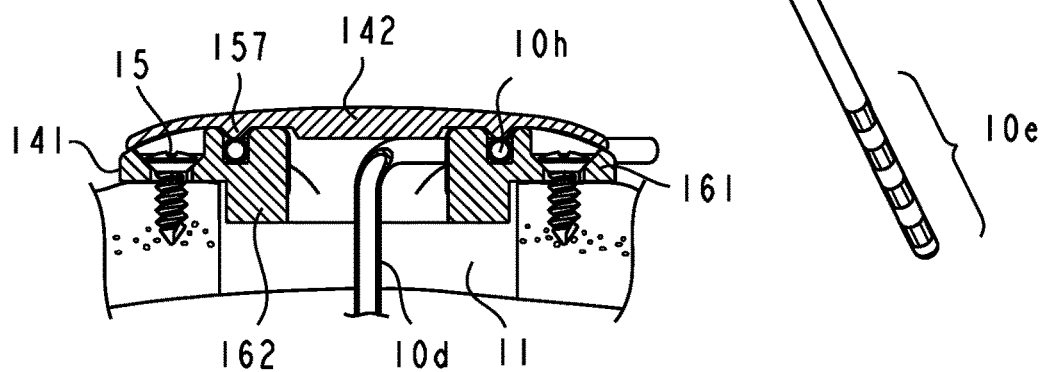
Figure 16C:
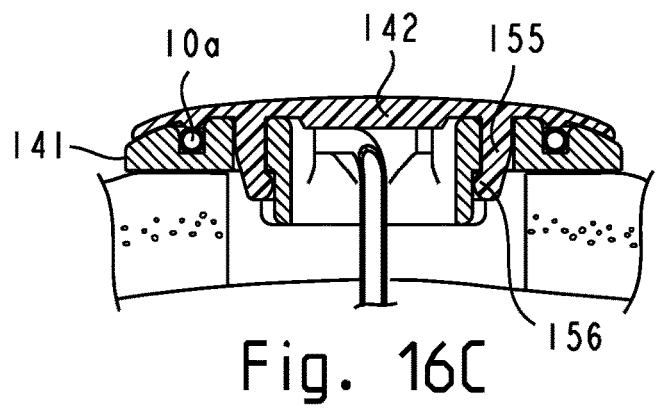

FIGS. 16A-16C show lead 10 implanted through burr hole 11 and secured at the exit from the burr hole by device 140. The upper body of base 141 forms a flange 161 with mounting holes 150 to enable attaching the base to the cranium with screws 15. The lower body 162 is sized to substantially center the base in the burr hole. Installation of the cover brings peripheral protrusion 157 in contact with the lead and thus helps to fully seat and maintain the lead in the peripheral grooves. The routing scheme of FIG. 16A, in combination with peripheral protrusion 157, minimizes the openings which could allow cerebrospinal fluid to leak through the device.

In the lead routing example of FIG. 16A, lead segment 10g exiting the burr hole is pressed into a radial retention groove 151 and transitioned into the peripheral retention grooves in the counterclockwise direction by routing lead segment 10b about inner protrusion 145. Lead segments 10a and 10h are pressed into peripheral grooves 152 and 153 to secure the lead by an interference fit. The lead is routed to the exit groove which is substantially codirectional with the radial retention groove taken by the lead, which maximizes the length of the lead segments retained in the peripheral grooves. The substantial length of the lead segments retained in the peripheral retention grooves enables an effective fixation and strain relief of the lead within the device. This assures that an inadvertent external pulling on the proximal portion of the lead extending from the device will not dislodge the distal end of the lead from the target location in the brain.

Figure 17A:
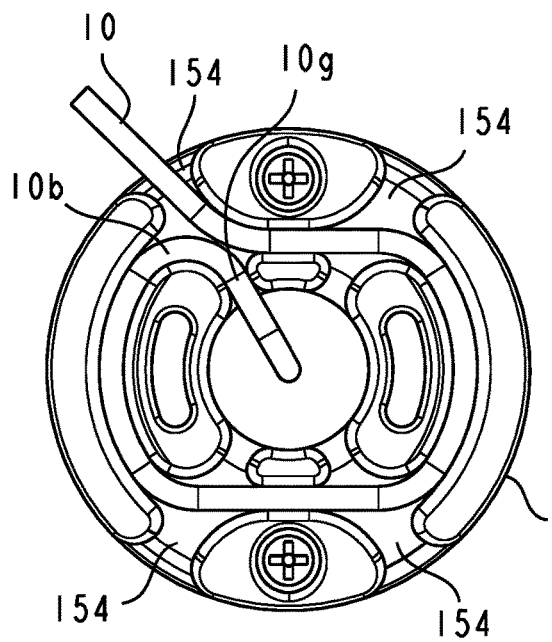
FIGS. 17A-17D show examples of lead routing in the radial and peripheral lead retention grooves of the device shown in FIG. 16A.
Figure 17B:
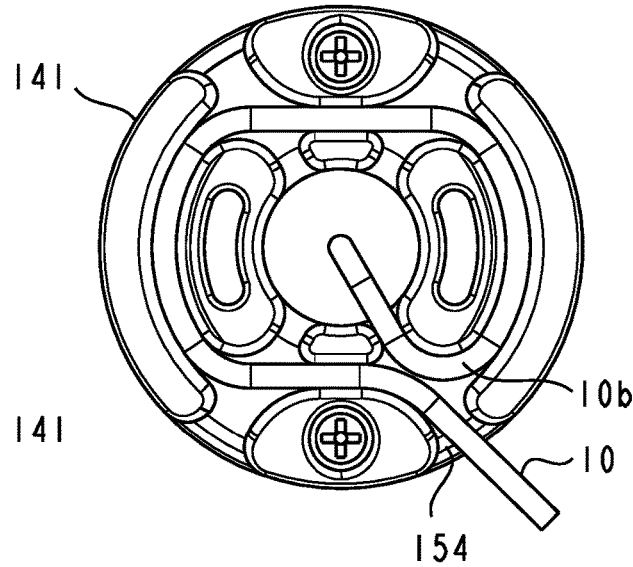
Figure 17C:
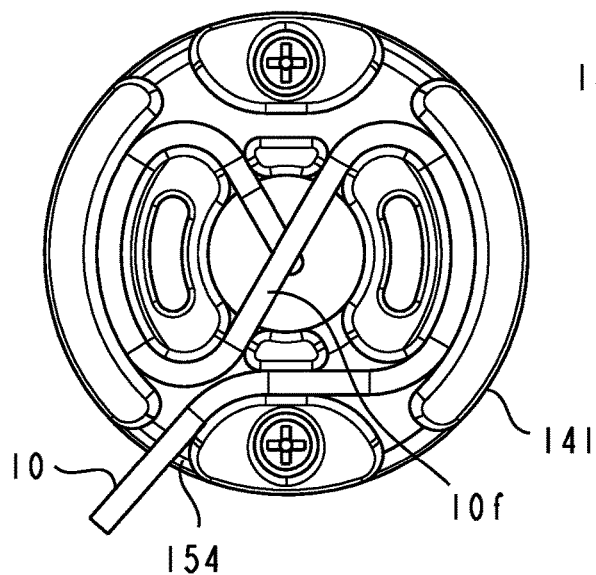

FIGS. 17A-17D illustrate how the lead can be routed to any desired lead exit 154. In FIG. 17A the lead is routed to the exit groove which is substantially codirectional with the radial retention groove taken by the lead, as in FIG. 16A. If the opposite lead exit direction is desired, the opposite radial retention grove 151 can be taken, and the lead can be transitioned into the peripheral grooves in the counterclockwise direction, as shown in FIG. 17B. The other two exit directions can be obtained by mirroring the first two, with the lead transitioned into the peripheral grooves in the clockwise direction. FIG. 17C illustrates a lead routing scheme wherein a lead segment 10f is routed diagonally across the central opening of the base and is retained in two additional radial retention grooves before returning to the peripheral grooves. Any other lead exit can be selected by rotating and/or mirroring this routing scheme.

Figure 17D:
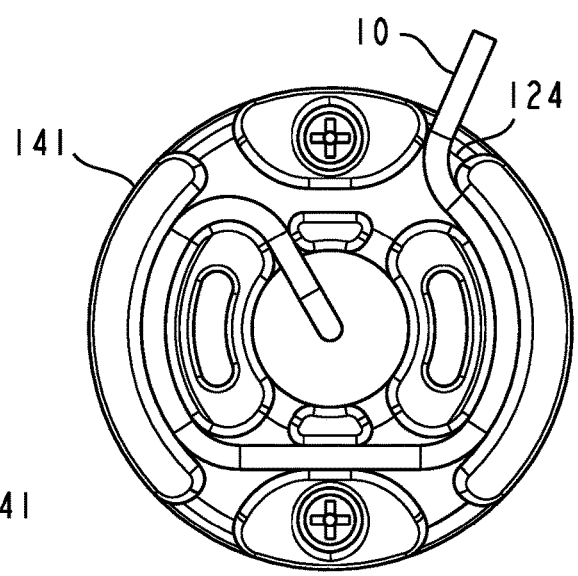
Figure 20A:
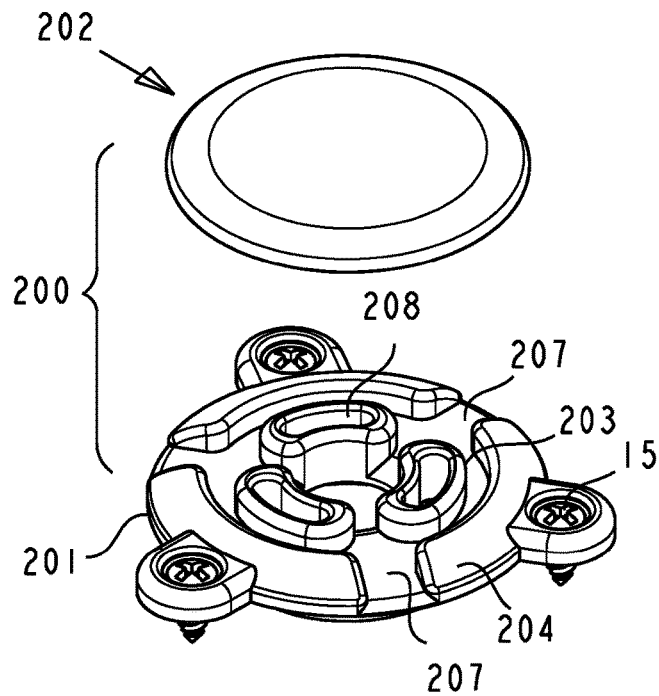
FIGS. 20A-21B show an embodiment of a device having radial and peripheral lead retention grooves formed by three sets of inner and outer protrusions.
Figure 20B:
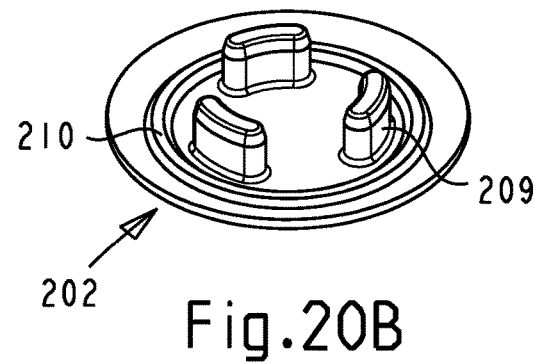
Figure 20C:
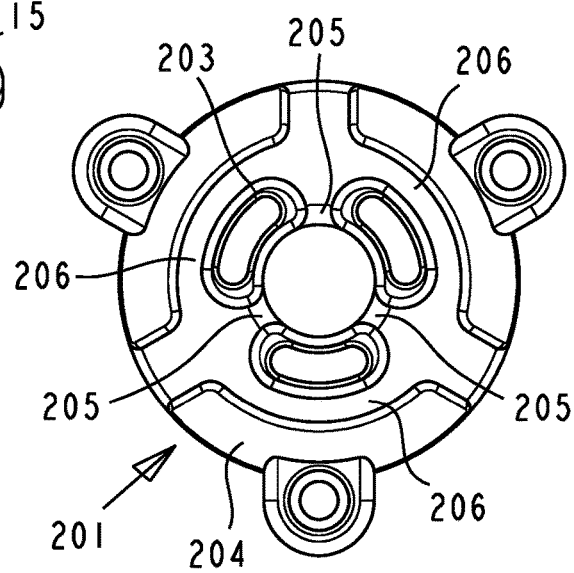

FIG. 17D illustrates still another routing scheme wherein the selected lead exit groove is angularly offset from the radial groove taken by the lead exiting the central opening. As with the other routing schemes, any of the three remaining lead exits can be taken by mirroring and/or rotating the routing scheme shown.

FIGS. 18A-19C show another embodiment of a device having radial and peripheral lead retention grooves for securing a lead at a burr hole. The device 180 comprises a base 181, a cover 182, and screws 15. The base has a central opening 183, which may be circular. The base further has inner protrusions 184 and 185 adjoining the central opening, and outer protrusions 186 and 187, adjoining the outer periphery of the base.

Radial lead retention grooves 188 are formed between the opposing side walls of inner protrusions 184 and 185, peripheral retention groves 190 are formed between the opposing side walls of inner protrusions 184 and outer protrusions 186, peripheral retention grooves 191 are formed between the opposing side walls of inner protrusions 185 and outer protrusions 187, and lead exit grooves 189 are formed between the opposing side walls of outer protrusions 186 and 187. Peripheral retention grooves 190 are wavy to more effectively lock the lead segments retained there. Inner protrusions 184 and/or 185 may further have holes 192 for receiving retention tabs of cover 182.

FIGS. 19A-19C show device 180 with lead 10 implanted and fixated in the device. The routing pattern through the radial and peripheral lead retention grooves depicted in FIG. 19A enables the longest length of lead segments 10a and 10h retained in the peripheral retention grooves. This pattern can be rotated and/or mirrored to select any of the four lead exit grooves 189. Other routing schemes can be selected as discussed above with reference to device embodiment 140. Cover 182 has tabs 193 configured to locate and retain the cover in the base. The cover may also have a peripheral protrusion 194 following the outline of the peripheral retention grooves, which maintains lead segments 10a and 10h fully inserted into the grooves.

Figure 21A:
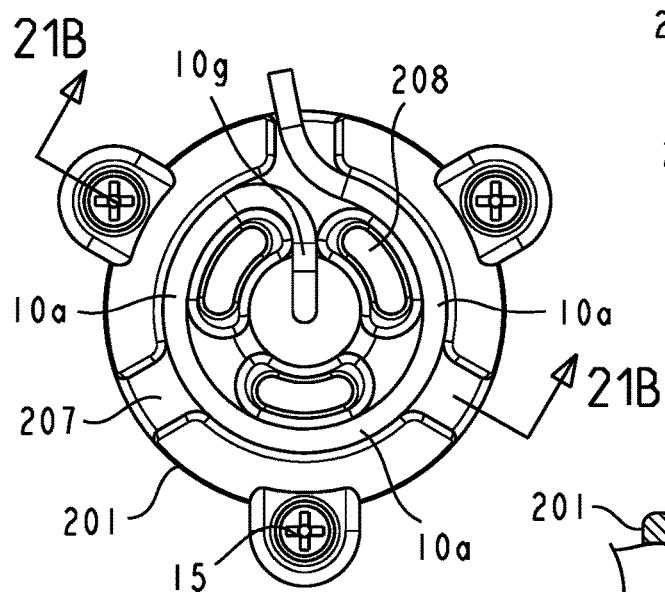
Figure 21B:
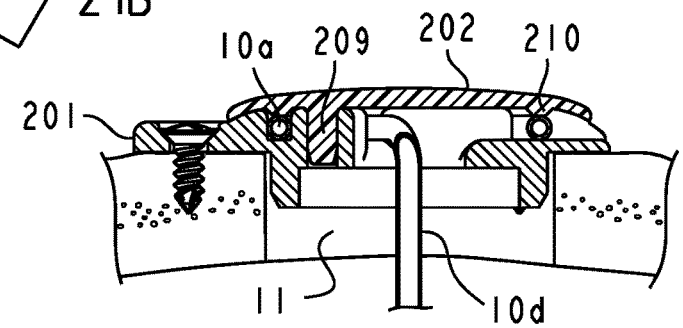
Figure 22A:
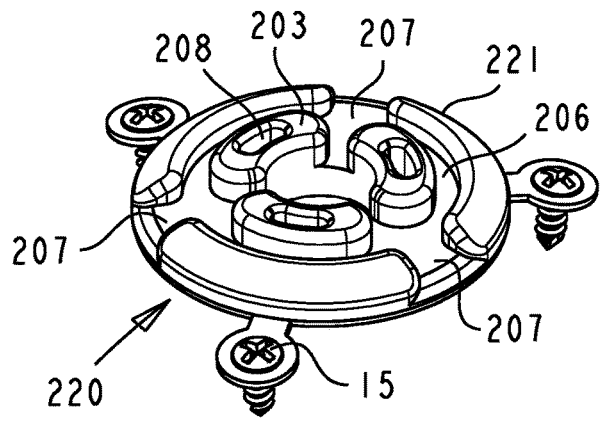
FIGS. 22A-23B show a device with radial and peripheral lead retention grooves comprising a base having insert molded mounting tabs.
Figure 22B:
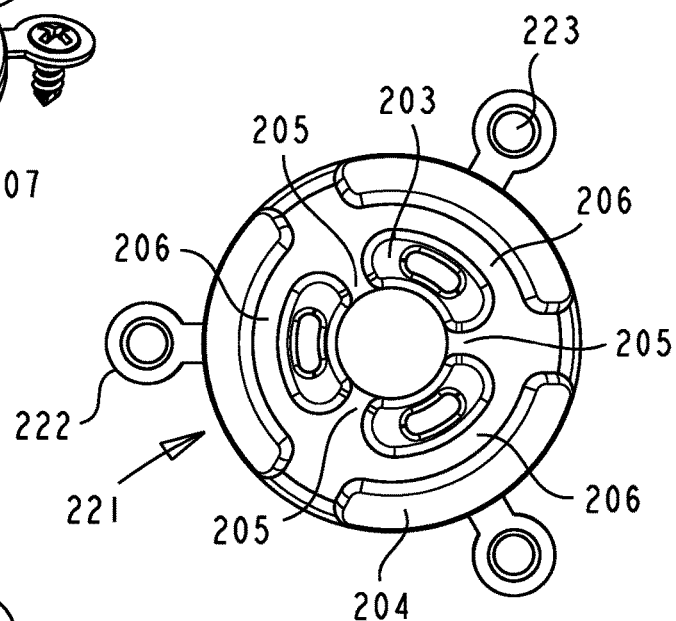
Figure 23A:
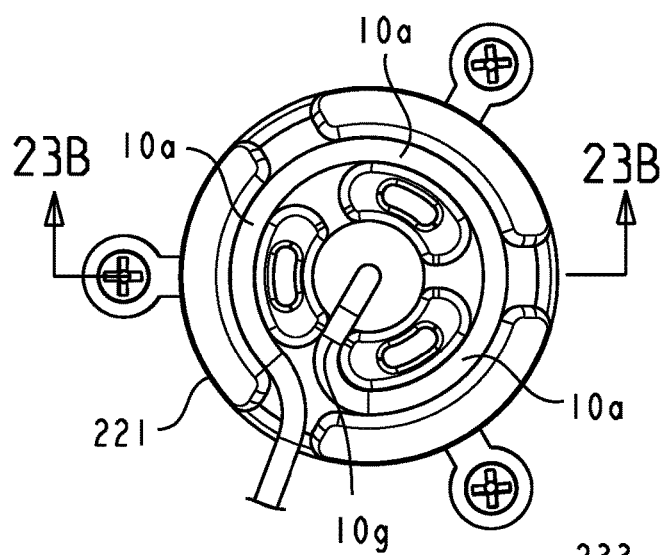
Figure 23B:
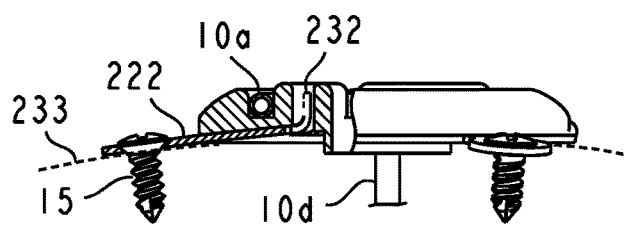
Figure 24A:
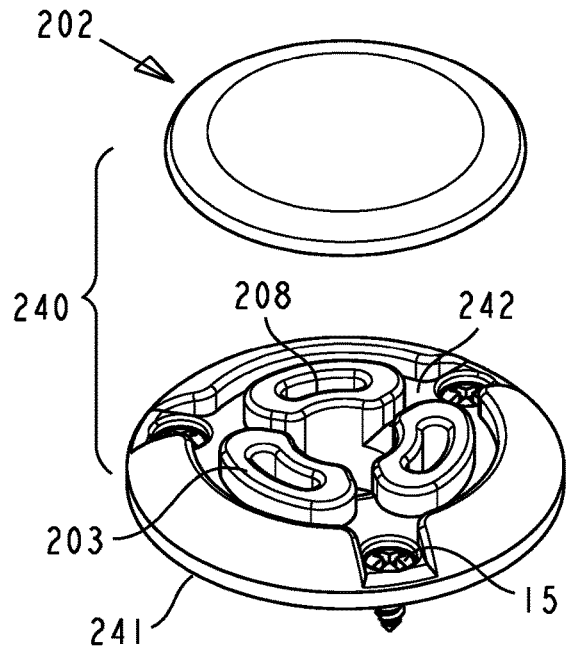
FIGS. 24A-25B show a device having mounting holes recessed under lead exit grooves.
Figure 24B:
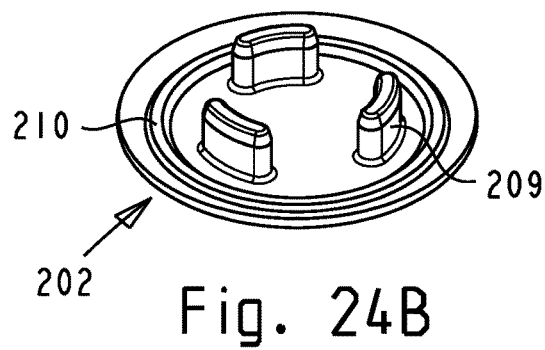
Figure 24C:
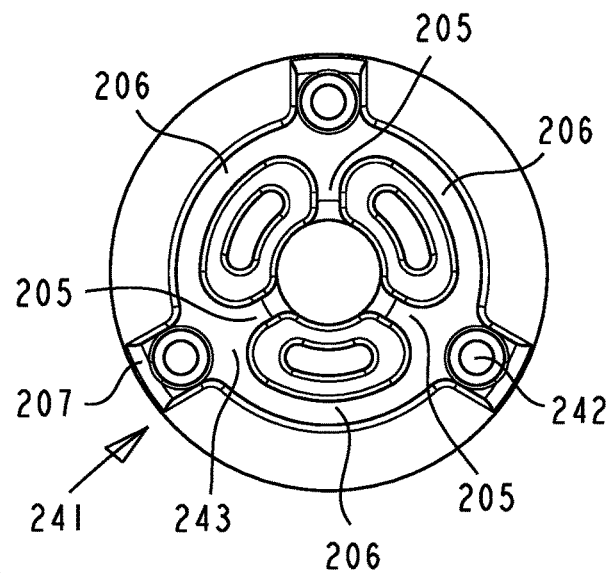

FIGS. 20A-21B show another embodiment of a lead fixation device with peripheral lead retention grooves. A device 200 comprises a base 201, screws 15, and cover 202. The base comprises three inner protrusions 203 and three outer protrusions 204. The side walls of these protrusions form three radial retention grooves 205, three peripheral retention grooves 206, and three lead exit grooves 207. The inner protrusions have apertures 208 for retaining cover 202. The cover comprises three tabs 209 configured for being retained in respective apertures 208 of the base. The tabs may have latching features as described with reference to device 140. The cover further has a protrusion 210, following the outline of the peripheral retention grooves in the base, configured to maintain segment 10a in the peripheral retention groove. FIG. 21B shows a cross sectional view of device 200 with lead segments 10a fixated in the peripheral retention grooves and cover 202 installed.

FIGS. 22A-23B show a device embodiment 220, having lead retention grooves similar to those in device 200. The device comprises a base assembly 221 and screws 15. The base assembly comprises insert-molded sheet metal mounting tabs 222 having mounting holes 223. The insert-molded portions 232 of the sheet metal can be imbedded in inner protrusions 203. The tabs can be factory preformed to approximate cranial curvature (represented in FIG. 23B by dotted line 233) and further adjusted during the surgical procedure. The device can be used with a small burr hole or drill hole and/or with the entire device seating above the cranial surface. The cover may be similar to cover 202 shown in FIG. 20B.

Figure 25A:
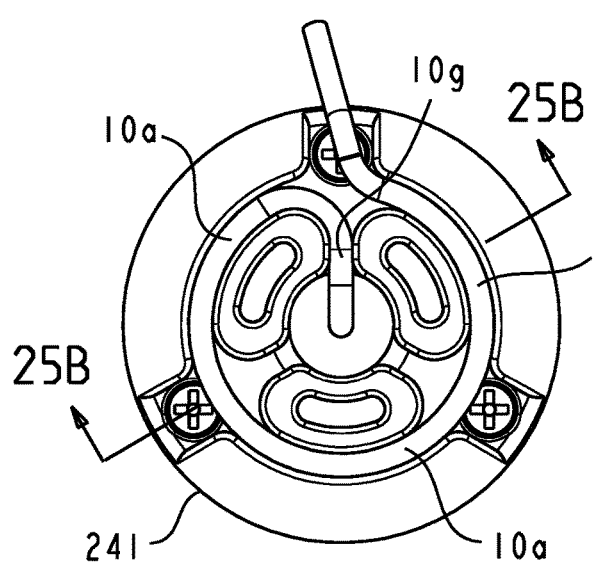
Figure 25B:
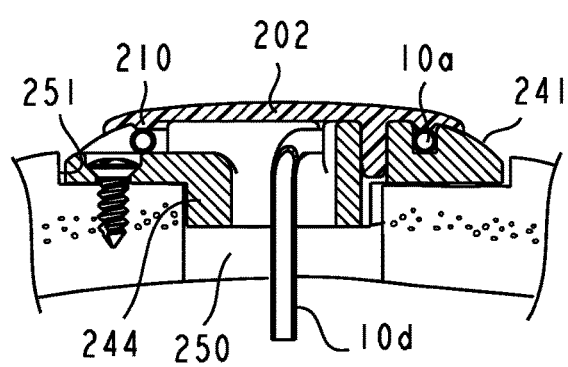
Figure 26A:
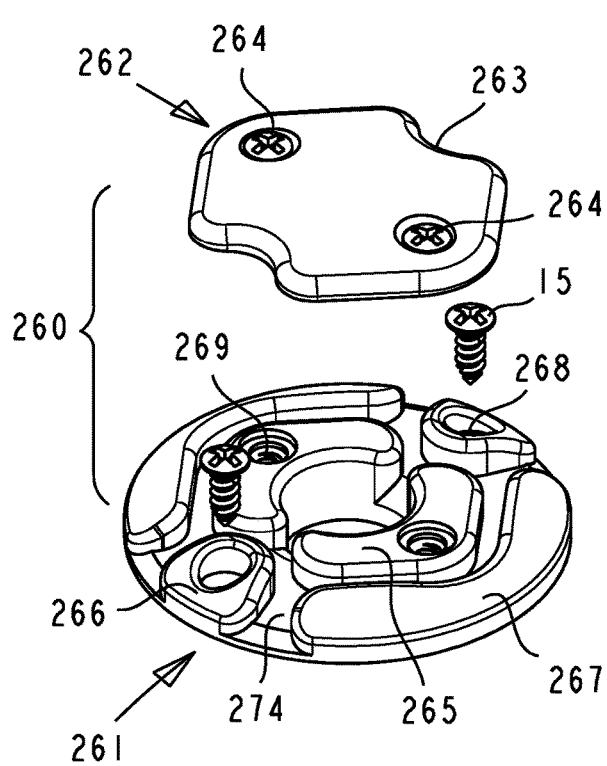
FIGS. 26A-27B show a device with an alternate configuration of radial and peripheral lead retention grooves and a screwed down cover.
Figure 26B:
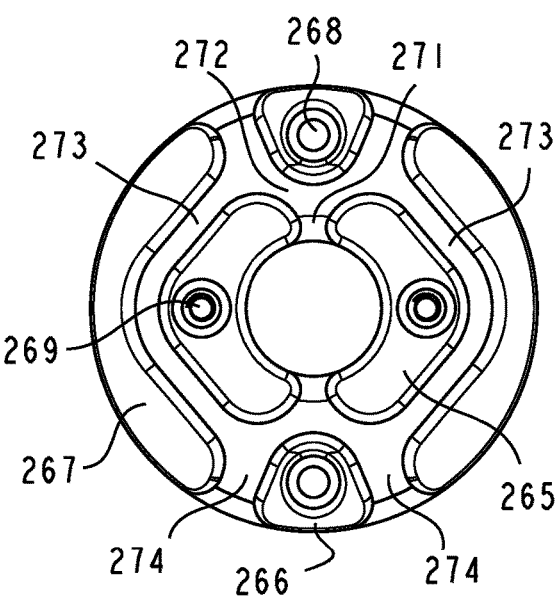

FIGS. 24A-25B show yet another device having lead retention grooves similar to those in device 200. A device 240 comprises a base 241, cover 202, and screws 15. Base 241 has mounting holes 242 located substantially within lead exit grooves 207. The heads of screws 15 are recessed from upper surface 243, so that lead segments 10a may be routed above them, as shown in FIGS. 25A-25B. This enables a smaller device e.g., having an outside diameter of 20 mm or less. The lower portion 244 of the base can also be sized for a smaller burr hole 250, e.g., having a diameter of 10 mm or less. The burr hole may have a counterbore 251 to reduce protrusion of the device above the cranial surface.

FIGS. 26A-27B show a device embodiment 260 comprising a base 261, screws 15, and a cover assembly 262. The cover assembly comprises a cover 263 and two captive screws 264. The base comprises two inner protrusions 265, two outer protrusions 266, and two outer protrusions 267. Outer protrusions 266 have mounting holes 268 for attaching the base to a cranium with bone screws 15. Inner protrusions 265 have threaded holes 269 for attaching the cover assembly to the base with captive screws 264. The inner and outer protrusions form a system of grooves comprising: radial retention grooves 271 between the opposing side walls of inner protrusions 265; peripheral retention grooves 272 between the opposing side walls of inner protrusions 265 and outer protrusions 266; peripheral retention grooves 273 between the opposing side walls of inner protrusions 265 and outer protrusions 267; and lead exit grooves 274 between the opposing side walls of outer protrusions 266 and 267.

Figure 27A:
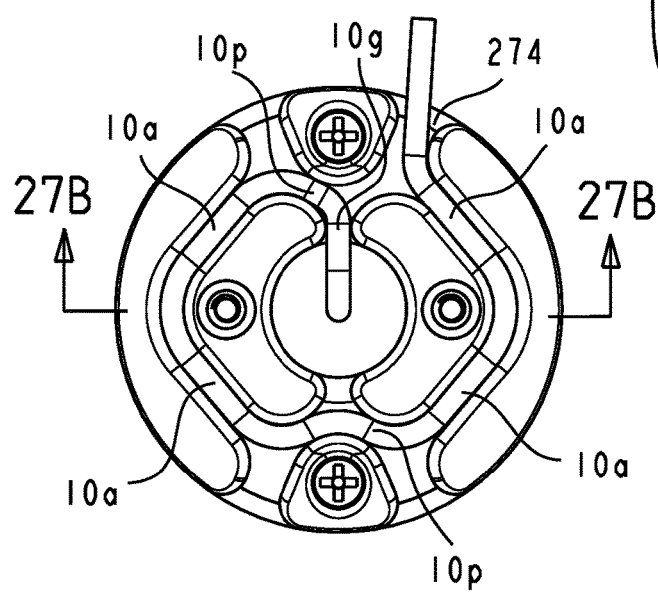
Figure 27B:
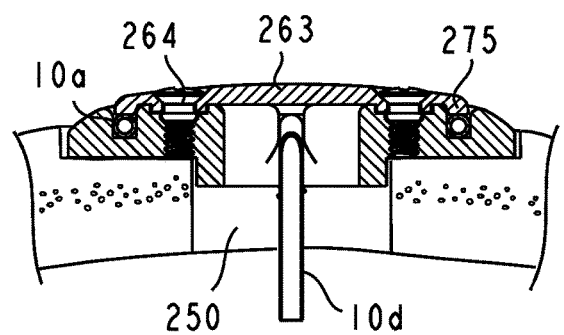

FIG. 27A shows lead segments 10p and 10a of the lead retained in peripheral retention grooves 272 and 273 in a wavy routing pattern, which aids in resisting slippage when an inadvertent external tension is applied to the proximal portion of the lead. The routing pattern can be rotated and/or mirrored to select any of the four lead exit grooves 274. FIG. 27B is a cross sectional view of device 260 with cover 263 clamped to the base with captive screws 264. A peripheral protrusion 275 on the underside of the cover positively maintains lead segments 10a and 10p in the peripheral grooves.

Figure 28:
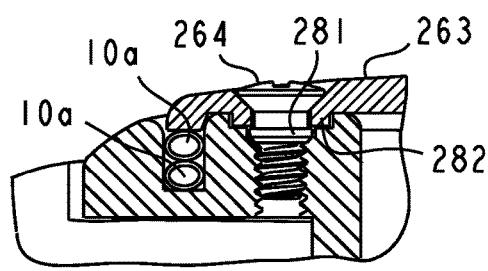
FIG. 28 show a cross sectional detail of a device with screwed down cover, adapted to retain two turns of a lead in the peripheral lead retention grooves.
Figure 34:
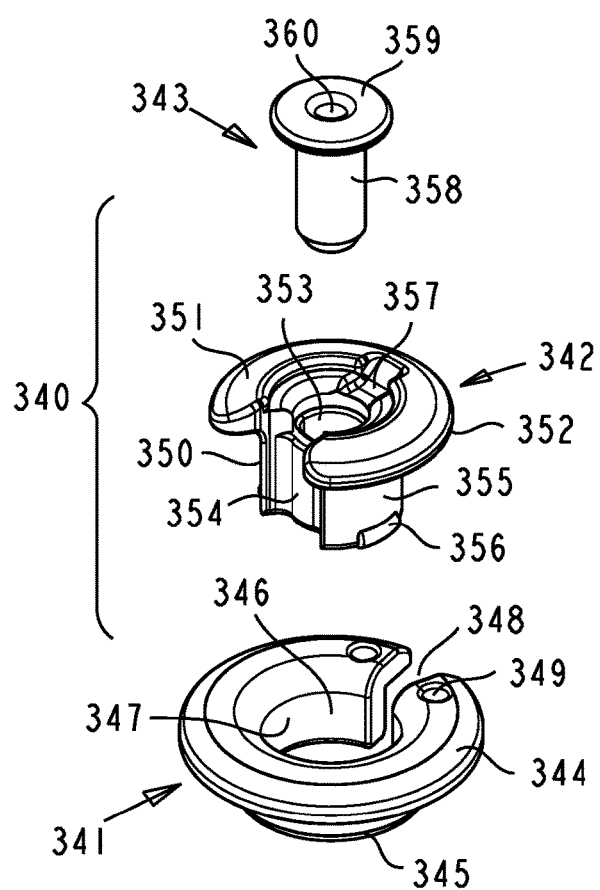
FIGS. 34-37B show a device comprising a resilient base having an integral off-center clamping wall activated by a pin-like plunger, wherein the lead is clamped against the inside wall of the central opening of the base.

FIG. 28 shows a cross sectional detail of an adaptation of device 260 for retaining more than one loop of the lead segments in the peripheral retention grooves. The larger scale of FIG. 28 also shows more clearly the features captivating screws 264 in the cover. The screws are pressed into respective retaining holes in the cover until a barb 281 of the screw is pushed through protrusions 282 on the underside of the cover the cover.

FIGS. 29A-30B show a device which can be inserted into a burr hole after the lead is introduced into the brain. A device 290 comprises a resilient base 291 and cover 292. The base has a radial slit 293 which allows the base to be placed directly above a burr hole after the lead is implanted and/or the cannula is present, as depicted in FIG. 9A. The base further has three inner protrusions 294 and three outer protrusions 295, forming radial retention grooves 296, peripheral lead retention grooves 297, and lead exit grooves 298. The inner protrusions further have apertures 299, which extend through the base.

The inner protrusions may also have slits 301 to make the base more flexible for squeezing the base for interference fit insertion into the burr hole. Holes 302 are provided to facilitate squeezing of the base with a tool, such as forceps. Alternatively, or in addition, cover tabs 304 may be configured to compress walls of lower portion 303 of the base against the inside of the burr hole to retain the base in the burr hole. The tabs may also be configured to further clamp lead segment 10g by bringing the opposing walls of the inner protrusions closer together, thus narrowing radial retention groove 296. The cover may further have a peripheral protrusion 305 on its underside, the protrusion following the outline of peripheral grooves 297 in the base, and configured to positively maintain lead segments 10a in the peripheral retention grooves.

FIG. 31 illustrates use of device 140 to secure two leads implanted through a single burr hole. Both leads 10(1) and 10(2) are passed through central opening 143 of base 141 and each lead has a segment 10g retained in a radial retention groove and segments 10a and 10h retained in the peripheral retention grooves. The two lead fixations are independent; the first lead can be secured in the device before the second lead is implanted. This minimizes the risk of affecting localization of the first lead when the second lead is implanted. To compensate for a shorter lead segments retained in the peripheral grooves, the side walls of the peripheral grooves may have ribs 310, extending upwardly from the bottom of the grooves, to enhance interlocking of the lead segments 10a with the peripheral grooves by introducing localized deformation of the lead.

FIGS. 32-33B show a device 320 which enables more than one loop of lead segments to be retained in two sets of substantially concentric peripheral retention grooves. The device comprises a resilient base 321, which has the clamp features and the peripheral grooves of device 80. However, in addition to outer protrusions 322, base 321 further comprises outer protrusions 323. The two concentric sets of outer protrusions form additional peripheral retention grooves 324 between them. The opposing walls of outer protrusions 322 form radial passages 325 to peripheral retention grooves 324. The opposing walls of outer protrusions 323 form lead exit grooves 326. Peripheral grooves may further have a lead retention lip 327, which makes it more difficult for the lead to back out of the groove. FIGS. 33A-33B show lead segments 10a clamped and retained in the first set of peripheral retention grooves as in device 80, and lead segments 10s retained in the second set of peripheral retention grooves. Plunger 17 and cover 60 may be the same as in device 80.

FIGS. 34-37B show a device 340 comprising a base 341, an interposer 342, and a pin-like plunger 343. The base comprises an upper portion 344 forming a flange, and a ring-shaped lower portion 345. The base further has a central opening 346 with inside wall 347. The base has a slit 348 extending through the lower and upper portions of the base to allow the base to be squeezed for insertion into the burr hole. Holes 349 can be used to insert the base into or remove the base from the burr hole with a tool such as forceps. Interposer 342 comprises a body 350 having a flange 351, a central aperture 353, a clamping wall 354, an outer wall 355, and snap-in protrusions 356. The flange has a perimeter edge 352. The interposer further has a cutout 357 which provides an access for a plunger removal tool. The plunger has a pin-like actuating tab 358 cooperating with the central aperture of the interposer, and a button shaped top portion 359 for pressing the plunger into the interposer. The top portion 359 may have a hole 360 for locating and retaining a cover (not shown) having a retaining tab on its underside.

Figure 35:
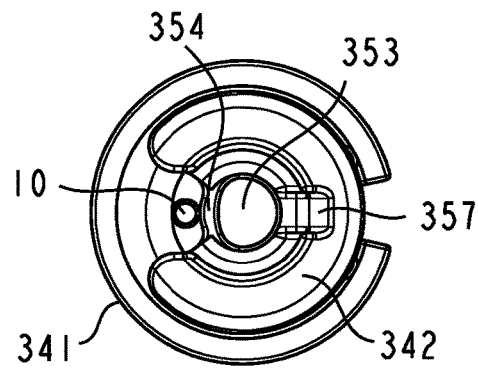

The base can be installed in the burr hole after the lead is introduced, preferably with the cannula still holding the lead. Alternatively, the base can be preinstalled in the burr hole prior to the introduction of the lead. After the lead is implanted and the cannula is raised, the interposer can be inserted into the central opening of the base until the snap-in protrusions 356 snap under the lower portion of the base. The interposer is inserted in a manner that brings the lead toward the side wall 347 of the central opening 346, without generating downward drag or traction on the lead. When the interposer is thus inserted, the lead remains uncompressed as shown in FIG. 35.

Figure 36:
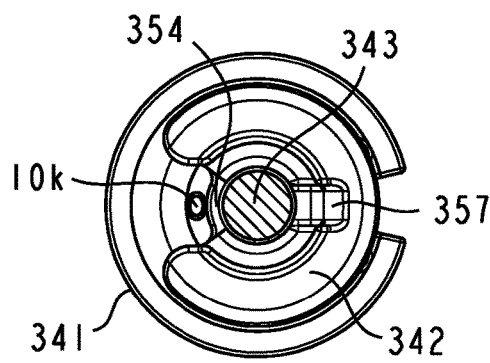
Figure 37A:
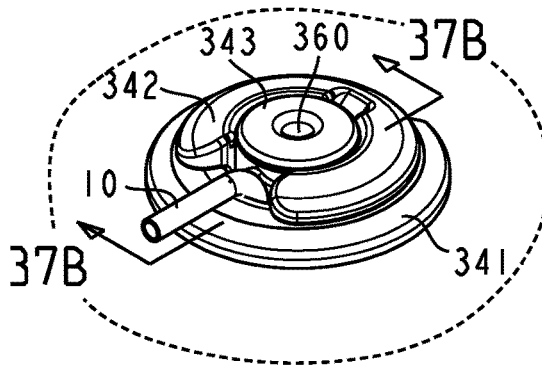
Figure 37B:
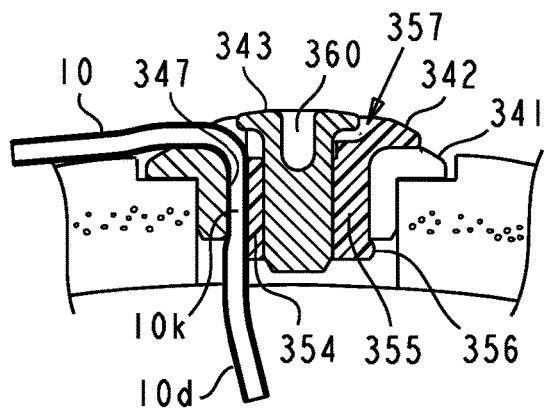
Figure 39:
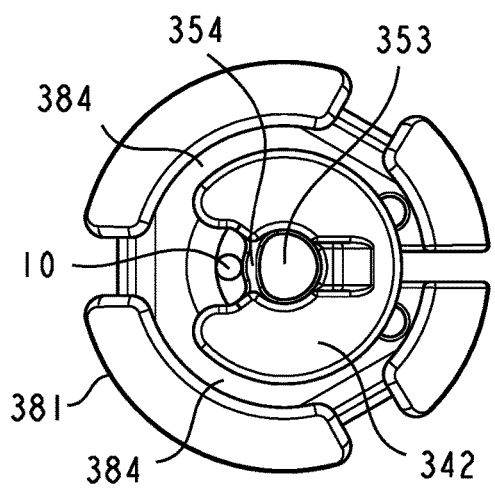
FIGS. 38-40B show a device comprising an integral off-center clamping wall activated by a pin-like plunger, further having peripheral lead retention grooves.
Figure 38:
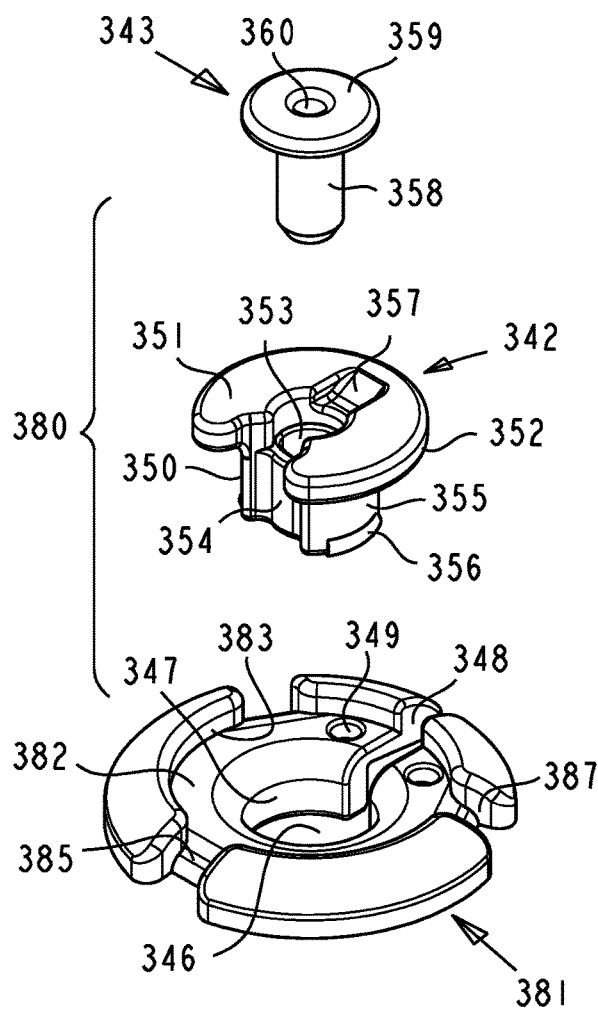

The clamp is activated by inserting plunger tab 358 into interposer aperture 353, which displaces clamping wall 354 radially to clamp the lead against side wall 347 of the central opening in the base, as shown in FIG. 36 and in the cross sectional view of FIG. 37B. FIGS. 37A-37B show a fully assembled device with a lead segment 10k clamped between clamping wall 354 of the interposer and side wall 347 of the base opening. The interposer can be further retained in the central opening of the base by using the plunger tab to compress the interposer outer wall 355 against side wall 347 of the base opening. A cover (not shown) having a centrally disposed tab may be attached to the plunger by pressing the tab into hole 360.

FIGS. 38-41 show a device 380 which is a variation of device 340 further providing peripheral lead retention grooves. Device 380 comprises a base 381, an interposer 342, and a plunger 343. The base comprises a top surface 382 and top inside wall 383 adjoining the perimeter of the top surface. As in device 340, the base has a slit 348 and holes 349 to enable the base to be squeezed for insertion of the base into the burr hole. The interposer and the plunger can be essentially as in device 340.

Figure 40A:
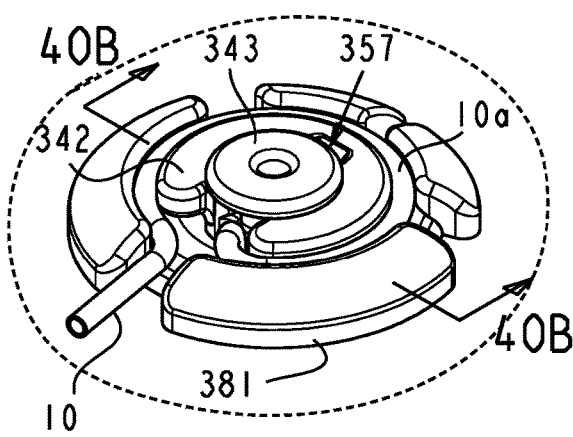
Figure 40B:
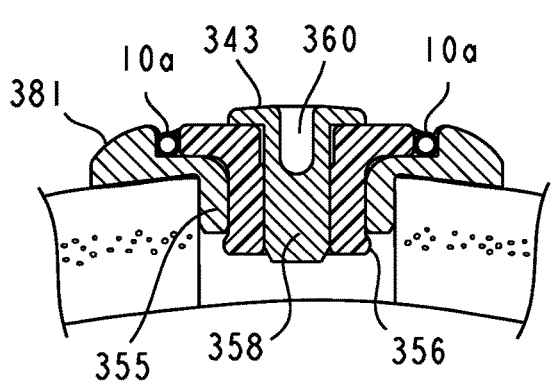
Figure 41:
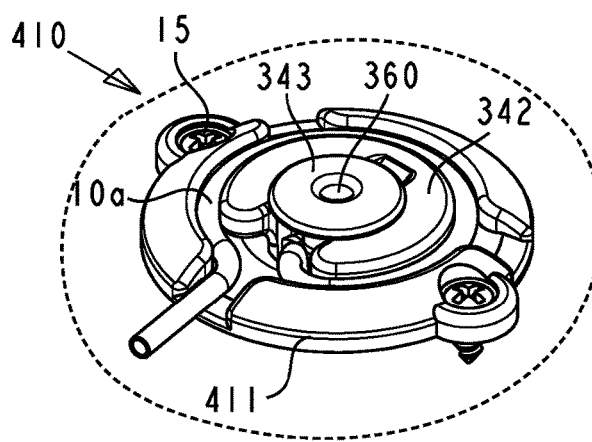
FIG. 41 shows a variation of the device of FIG. 40A, comprising a base attached to the cranium with bone screws.

After the lead is secured by the clamp as described above with reference to device 340, peripheral lead retention grooves 384 are formed between perimeter edge 352 of the interposer flange and the opposing top inside wall 383. The base further has three lead exit grooves 385 to enable lead exit from the device in a desirable direction. FIGS. 40A-40B show the lead secured by the clamp and lead segments 10a further retained in peripheral grooves 384. FIG. 41 shows a device 410, which is an embodiment of device 380, having a base 411 adapted for attachment to a cranium with screws 15. A cover (not shown) having a centrally disposed retaining tab may be attached to the plunger by pressing retaining tab 358 into hole 360.

FIGS. 42-60B show devices having a clamp wherein the clamping walls are integral parts of the base. The clamping walls are portions of elastic beams which are integral parts of the base. The clamp is activated by a plunger having tabs which displace the clamping walls inwardly, toward each other, to clamp the lead. The displacement is reversible due to the elasticity of the beams. FIGS. 42-53B show devices comprising a substantially circular base having integral arcuate beams. FIGS. 54A-59B show devices comprising an elongated base having integral double-ended beams.

FIG. 42 shows a device 420 comprising a base 421, a plunger 422, a cover 423, and screws 15. The base comprises two arcuate beams 424 integrally attached to the base. Each beam has a clamping wall 425 on its free end. The base further comprises a flange 426, lead exit grooves 427, mounting holes 428, and cutouts 429 for locking the cover to the base. Plunger 422 comprises actuation tabs 31, top portion 32 having perimeter edge 33, actuating surfaces 34, holes 36, and slot 26, which are similar in form and function to those described above with reference to device 13. Cover 423 comprises locking tabs 430, and an exit groove covering flap 431.

The base is further illustrated in FIGS. 43A-B. Each arcuate beam 424 has a fixed end 432 attached to an inside wall 433 of the base. The clamping walls are centrally disposed in the base forming a slot 434. The arcuate beams and the clamping walls define apertures 435 for receiving the actuating tabs 31 of the plunger. Each clamping wall has a clamping surface 436, facing the slot, and an actuation surface 437, facing the aperture. The clamping surface may have grip enhancing protrusions or texture 438, shown symbolically in FIG. 42. When plunger tabs 31 are pressed into respective apertures 435 of the base, clamping walls 425 are displaced toward each other to securely captivate lead segment 10c as shown in the cross sectional view of FIG. 44B. After the clamp is activated, lead segments 10a can be further retained in the peripheral retention grooves formed between top inside wall 439 of the base and the opposing perimeter edge 33 of the plunger, as described above with reference to device 13. FIG. 44A shows device 420 assembly with the lead fully secured. FIG. 44B shows a cross sectional view of a fully assembled device with cover 423 installed.

Figure 45:
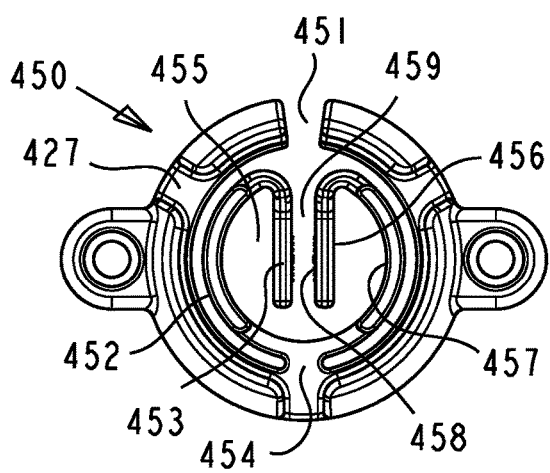
Figure 46:
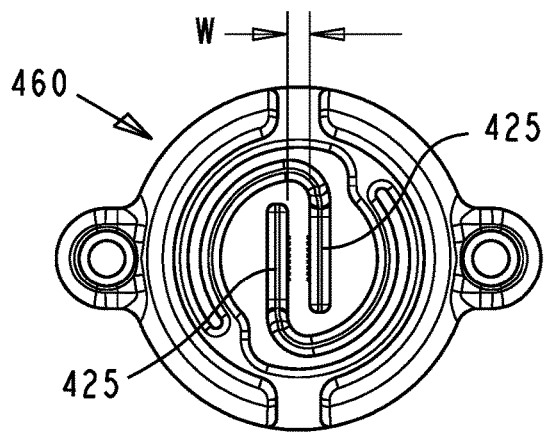

FIG. 45 shows a base 450 which can be inserted into a burr hole after the lead is implanted. The base has a slit 451 to allow placement of the base in a burr hole with a cannula present. The base has integral arcuate beams with clamping walls at the free ends, as the base in device 420, but in a modified configuration. Arcuate beams 452 and clamping walls 453 are symmetric with respect to each other and have a common fixed end 454. Each aperture 455 is formed substantially between actuation surface 456 and an inner arcuate surface 457 of the respective beam. Clamping surfaces 458 form a slot 459 aligned with slit 451, to facilitate side entry of the base to a position directly above the burr hole when the cannula is present. The base can be used with plunger 422 as in device 420 described above. In addition, apertures 455 may be sized to receive actuation tabs 31 with an interference, designed to increase retention of the plunger in the base.

Figure 47:
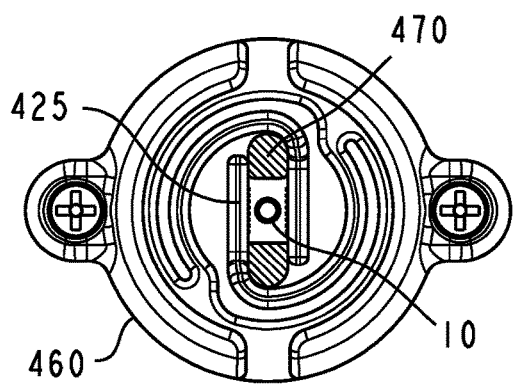
Figure 48:
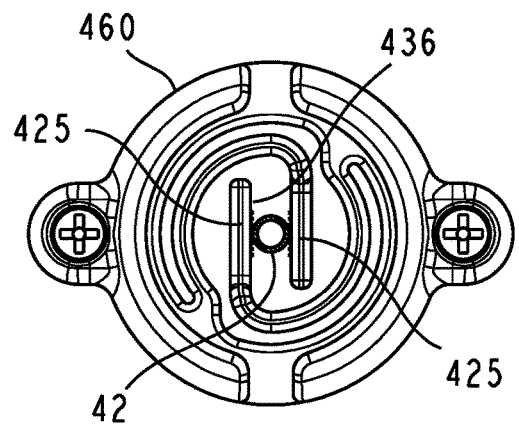
Figure 49:
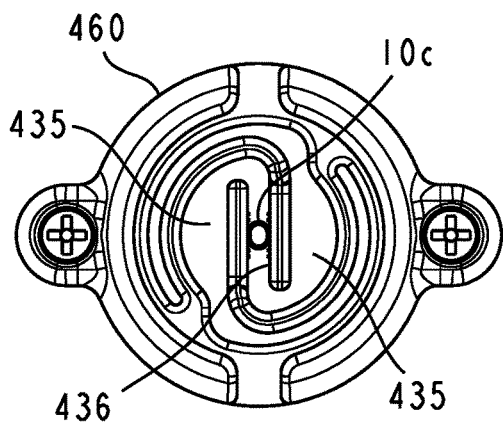
Figure 50:
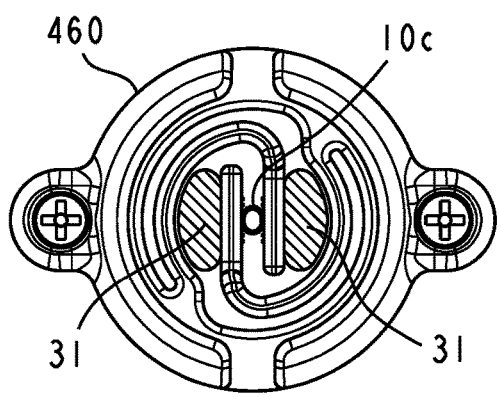
Figure 51:
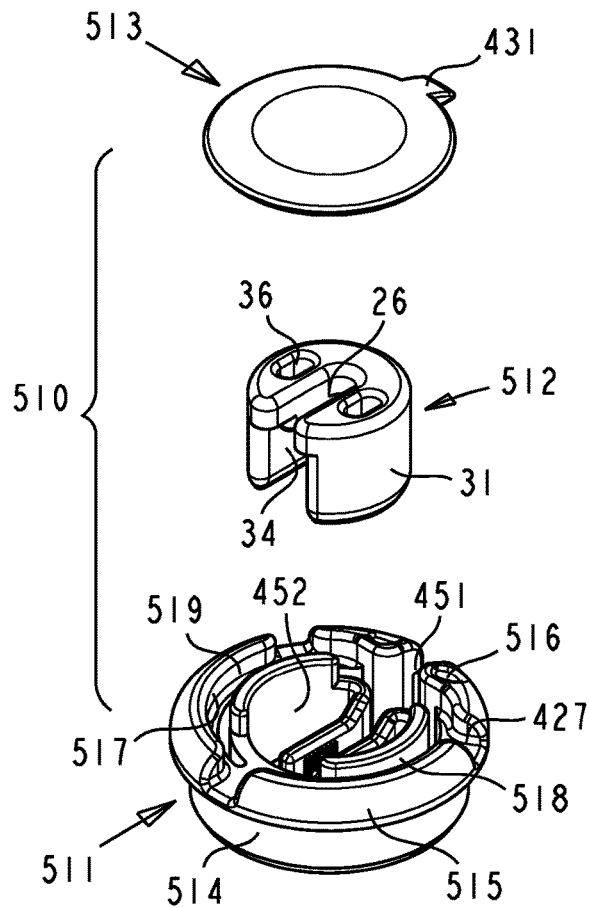
Figure 52A:
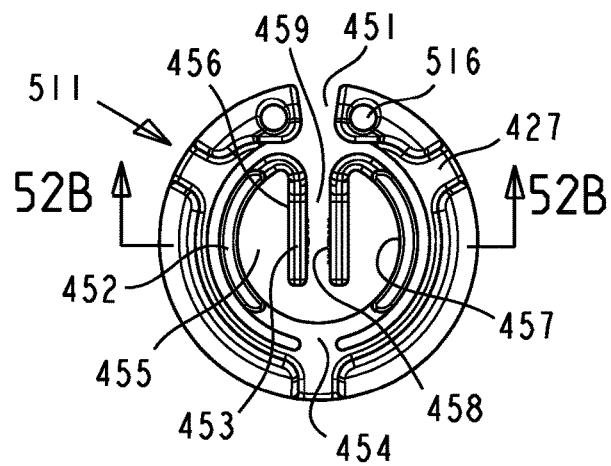
Figure 52B:
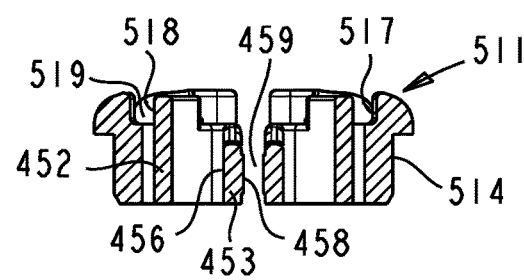

FIGS. 46-50 illustrate a base 460 with a naturally active clamp, wherein the width W of the slot in a free state (normal or natural state) is smaller than the diameter of the lead. The stiffness of the beams and the width of the slot are designed to clamp the lead in the natural state. The clamping walls are elastically spread apart to allow unimpeded insertion of the lead and/or a cannula, and are subsequently allowed to return to the natural state to clamp the lead. The clamping walls can be spread with a disposable insert 470, as shown in FIG. 47. Alternatively, the clamping walls can be spread by cannula 42, as shown in FIG. 48. In this case the base must be placed on a cannula before the lead is introduced, unless a slitted base, such as base 450 is used. After insert 470 and/or cannula 42 are removed, the clamping surfaces naturally move toward each other, thus clamping the lead, as shown in FIG. 49. A plunger can be used to further secure the lead by immobilizing the clamping walls with plunger actuating tabs 31 shown in cross section in FIG. 50.

Figure 53A:
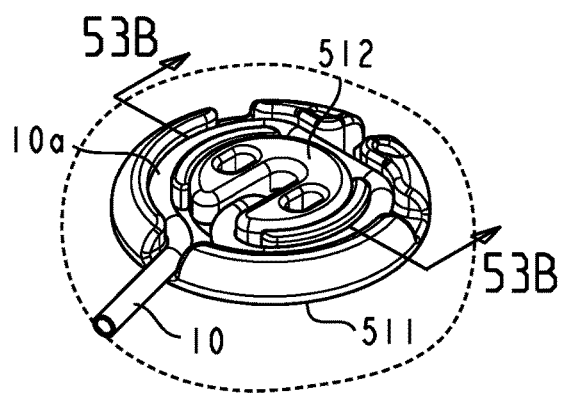
Figure 53B:
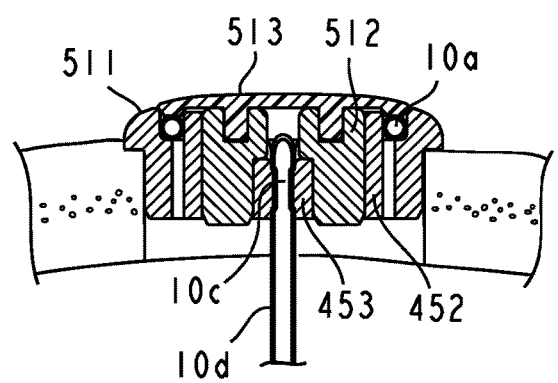

FIGS. 51-53B show a device 510 having a base similar to base 450 described above, but adapted for installation in a burr hole without using clamping hardware, such as bone screws. The device comprises a base 511, a plunger 512, and a cover 513. The base has a split ring shaped outer wall 514 configured for mounting in a burr hole and a flange 515 configured for seating the base on a cranium. Slit 451 and holes 516 allow the base to be compressed for insertion into the burr hole. The base further has a top inside wall 517 and the arcuate beam has an upwardly extended width portion 518. The opposing surfaces of top inside wall 517 and extended width portion 518 are substantially concentric and are spaced to form peripheral lead retention grooves 519. The clamp features and functionally can be as described above with reference to device 420. FIGS. 53A-B show device 510 with lead segment 10c clamped between clamping walls 453 of the base, and lead segments 10a further retained in the peripheral grooves 519.

Figure 54A:
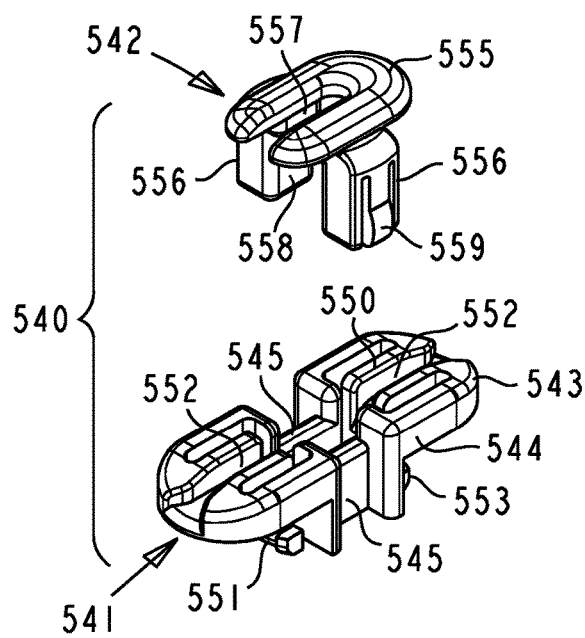
Figure 54B:
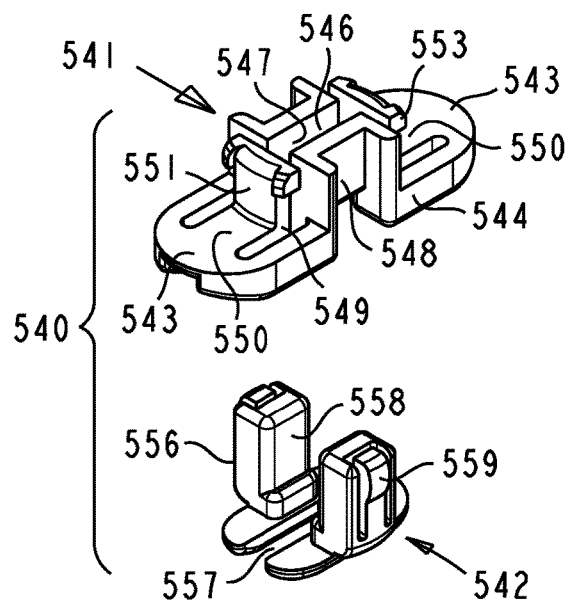
Figure 55:
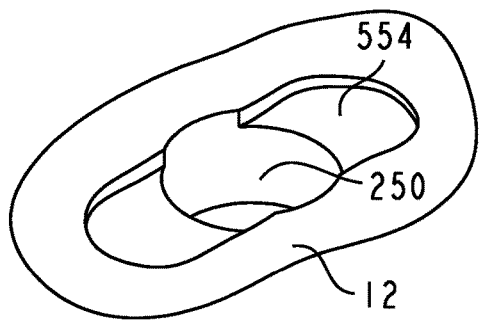

FIGS. 54A-B show a device 540 which can be used with small burr holes or drill holes, e.g., having a diameter of about 8 mm. The device comprises a base 541 and a plunger 542. The base has an elongated upper body with end portions 543 configured to seat on a cranial surface. The base further comprises two double-ended beams 544, each having fixed ends attached to the respective end portions of the base. Each beam has a clamping wall 545 at its midsection. The clamping walls are recessed inwardly to form a slot 546 for receiving a lead, and have downward extensions configured to be accommodated in the burr hole. Each clamping wall comprises a clamping surface 547 on the side facing the slot, and an actuation surface 548 on the other side. The clamping surfaces may have a grip enhancing protrusions or texture, similar to feature 438 shown in FIG. 42.

The base further comprises angled beams 549, each middle beam comprising an upper portion 550 attached to a respective end portion of the base, and an angled end 551 extending downwardly into the burr hole and configured to locate and retain the base in the burr hole. The angled end 551 may form close to a right angle with the upper portion 550. The upper portion of the middle beam comprises a radial (with respect to the burr hole) lead retention groove 552 having a width sized to retentively receive the lead segment exiting the clamp. The angled end of the middle beam may have protrusions 553 configured to create an interference fit against the inside wall of the burr hole. The cranial surface adjacent to the burr hole may have planarized surfaces or recesses 554 to reduce device protrusion above cranial surface 12. Alternatively, the undersides of the upper portions of the base may be profiled to better comply with the cranial curvature. Since the width of the base can be as small as the diameter of the burr hole, i.e., about 8 mm, the narrow elongated base with profiled undersides can be rotated about the burr hole for optimal match with the local cranial curvature.

Plunger 542 comprises a top portion 555 and two actuating tabs 556 attached to the top portion. The top portion has a slot 557 which allows the plunger to be positioned directly above the burr hole with the lead and/or cannula present. Each actuating tab comprises an actuating surface 558 which is imposed on actuation surface 548 of the respective clamping wall when the clamp is activated. The actuation tabs further have resilient retention tabs 559 designed to provide an interference fit for retaining the plunger in the burr hole, as shown in the cross sectional view of FIG. 57B.

Figure 56:
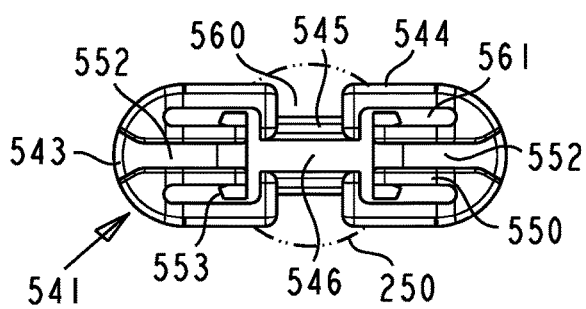
Figure 57A:
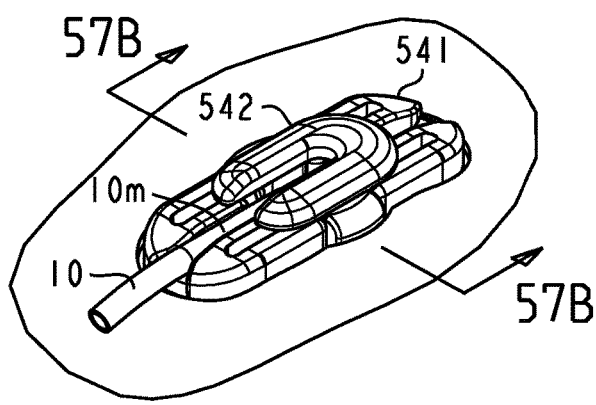
Figure 57B:
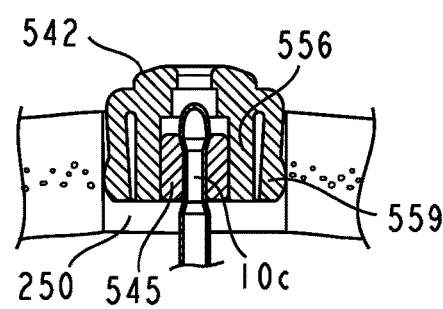

When plunger tabs 556 are pressed into respective apertures 560 formed between actuation surfaces 548 and the inside wall of the burr hole 250, represented in phantom line in FIG. 56, clamping walls 545 are deflected toward each other to securely captivate segment 10c of the lead positioned in slot 546, as shown in the cross sectional view of FIG. 57B. After the clamp is activated, the lead segment 10m can be further retained in a radial lead retention groove 552, as shown in FIG. 57A. If desired, a thin elastomeric boot (not shown) can be placed over the device. The boot may have retaining protrusions on its underside, fitting unoccupied retention groove 552 and/or slits 561 between double ended beams 544 and middle beams 549.

FIGS. 58-60B show a device 580, which is a variation of device 540, adapted for mounting to a cranium with bone screws or equivalent fasteners. Device 580 comprises a base 581, plunger 542, and two screws 15. End sections 582 of the base comprise mounting holes 583. The base further comprises radial (with respect to the burr hole) lead retention grooves 584, and peripheral lead retention grooves 585. After the lead is secured between clamping walls 545, as in device 540 shown in FIG. 57B, lead segment 10m is further retained in radial lead retention groove 584, and lead segment 10n is further retained in peripheral lead retention groove 585. In other respects, device 580 may be the same as device 540.

The components of the devices described herein may be made from biocompatible grades of polymers and metals suitable for implantation in a human cranium. The rigid and substantially rigid components, e.g., bases 14, 141, 181, 201, 221, 241, 261, and 411, plungers 17, 112, 343, 422, 512, and 542, and covers 142, 263, and 292, can be made from polymers such as polyetheretherketone (PEEK), nylon, and elastomers such as silicone and polyurethane having durometer of about 50 Shore D or higher. If desired, rigid components can also be made from metals such as Titanium, Titanium alloys, and stainless steel. The components that have elastically deflectable features, e.g., bases 341, 381, 421, 460, 511, 541, and 581, and covers 142 (with latches) and 423 can be made from polymers such as PEEK and nylon, and elastomers such as silicone and polyurethane having durometer of about 50 Shore D or higher. The components having resilient or compressible features, e.g., bases 81, 111, 291, and 321, interposers 16, 70, and 342, and covers 60, 113, 142 (without latches), 182, 202, and 513, can be made from elastomers such as silicone and polyurethane having durometer of about 50 Shore A. However, different materials and durometers than those specified above may also produce good results.

While the disclosed lead fixation devices have been described by means of specific embodiments, numerous modifications and variations known to those skilled in the art or disclosed may be employed without departing from the scope of the invention set forth in the claims. For example, clamp features described as integral part of a base may be separate parts permanently assembled in the base. The devices depicted as having only peripheral lead retention grooves may be modified to include a clamp. The width and height of the retention grooves need not be constant as depicted, but may vary along the length of the grooves. The actuation surfaces of clamping walls and the cooperating actuating surfaces of the plunger tabs may be profiled to optimize their engagement. The materials, shapes, and sizes of all parts may be adapted to a particular need. The devices disclosed in the context of deep brain stimulation leads are also applicable for fixation of catheters, or similarly shaped devices.

As to every element, it may be replaced by one of multiple equivalent alternatives, only some of which are disclosed in the specification. Thus the scope of the invention should be determined not by the examples or specifics given, but by the appended claims and their legal equivalents.

I claim:

1. A device having a clamp for securing a lead implanted through a burr hole into a brain of a patient, the device comprising:
   (A) a base configured for being mounted at the burr hole, the base comprising a central opening having an inside surface;
   (B) an interposer comprising a lower portion having an outer wall, the outer wall cooperating with the inside surface to locate the interposer in the central opening of the base; the interposer further comprising at least one clamping wall, the clamping wall having a clamping surface on one side and an actuation surface on the other side; the interposer further comprising at least one aperture adjoining the clamping wall, the aperture providing an access to the actuation surface of the clamping wall;
   (C) a plunger comprising a top portion and at least one actuating tab extending from the top portion, the actuating tab configured to be received in the aperture of the interposer; the actuating tab having an actuating surface cooperating with the corresponding actuation surface of the clamping wall;
   whereby when the actuating tab is pressed into the interposer aperture, the clamping wall is resiliently displaced by the actuating tab in the direction normal to the clamping surface, thus activating the clamp.

2. The device of claim 1 wherein the outer wall of the interposer comprises snap-in protrusions and the base comprises an undercut; wherein when the interposer is seated in the central opening of the base, the snap-in protrusions snap behind the undercut to retain the interposer in the base.

3. The device of claim 1 wherein: the base has a top surface and a top inside wall adjoining the top surface; the top portion of the plunger has a perimeter edge; wherein after the clamp is activated, the perimeter edge of the plunger and the opposing top inside wall of the base form at least one peripheral retention groove, configured to retentively secure the lead.

4. The device of claim 1 wherein the base has a top surface and a top inside wall adjoining the top surface; the interposer comprises a flange having a perimeter edge; wherein when the interposer is assembled in the base, the perimeter edge of the interposer flange and the opposing top inside wall of the base form at least one peripheral retention groove configured to retentively secure the lead.

5. The device of claim 1 further including a cover wherein the cover has at least one retaining tab and the top portion of the plunger has at least one retention hole; wherein the cover tab is configured to be retentively received in the plunger hole, thus attaching the cover to the plunger.

6. The device of claim 1 wherein the clamping wall is opposed to the inside surface of the base opening and the interposer aperture adjoining the clamping wall is substantially centered in the interposer; wherein when the actuating tab is pressed into the aperture, the clamping wall is displaced toward the inside surface to clamp the lead against the inside surface of the base opening.

7. The device of claim 1 wherein the central opening of the base is substantially circular and the outer wall of the interposer is configured to allow rotation of the interposer in the central opening of the base, whereby the interposer can be rotated to a desired angular orientation with respect to the base before the clamp is activated.

8. The device of claim 1 wherein: the interposer has two opposing clamping walls forming a slot for receiving the lead, each clamping wall having the clamping surface on the side facing the slot and the actuation surface on the other side; the interposer further comprises two apertures, each aperture adjoining the respective clamping wall and providing the access to the actuation surface of the respective clamping wall; and the plunger comprises two actuating tabs, each tab configured to be received in the respective aperture of the interposer; whereby when the plunger actuating tabs are pressed into the respective apertures of the interposer, the clamping walls are displaced toward each other to activate the clamp.

9. The device of claim 8 further including a cannula, wherein the clamp is activated on the cannula positioned in the slot, and wherein the clamping action is transferred to the lead after the cannula is retracted from the slot.

10. The device of claim 8 wherein each interposer tab has an outer surface, wherein when the clamp is activated, the outer surface of the plunger tab compresses the outer wall of the interposer against the inside surface of the base to lock the interposer in the central opening of the base.

11. The device of claim 8 wherein: the top surface of the base has cutouts adjoining the exit grooves; the interposer comprises a flange having a bevel; and the top portion of the plunger comprises an underside; wherein when the device is assembled, the cutouts and the bevel form an access to the underside of the top portion of the plunger, whereby the plunger can be removed from the interposer with a prying tool.

12. A device having a clamp for securing a lead implanted through a burr hole into a brain of a patient, the device comprising:
(A) a base configured for being mounted at a cranial burr hole, the base comprising two opposing clamping walls forming a slot for receiving the lead, each clamping wall having a clamping surface on the side facing the slot and an actuation surface on the other side; the base further forming two apertures, each aperture adjoining a respective clamping wall and providing an access to the actuation surface of the respective clamping wall; and
(B) a plunger comprising two actuating tabs, each actuating tab configured to be received in a respective aperture;
whereby when the plunger tabs are pressed into the respective apertures, the clamping walls are displaced toward each other, thus activating the clamp.

13. The device of claim 12 wherein: the base comprises a top inside wall; and the plunger comprises a top portion having a perimeter edge; wherein after the clamp is activated, the perimeter edge of the top portion of the plunger and the opposing top inside wall of the base form at least one peripheral retention groove configured to retentively secure the lead.

14. The device of claim 12 further including a cannula, wherein the clamp is activated on the cannula positioned in the slot, and wherein the clamping action is transferred to the lead after the cannula is retracted from the slot.

15. The device of claim 12 wherein: the base has an outer wall: the burr hole has an inside wall; and each plunger tab has an outer surface; wherein when the clamp is activated on the lead positioned in the slot, the outer surfaces of the tabs compress the outer wall of the base against the inside wall of the burr hole, thus retaining the base in the burr hole.

16. The device of claim 12 wherein the base has a slit substantially aligned with the slot, wherein the slit enables the base to be positioned directly above the burr hole after the lead is implanted, and to be squeezed for insertion into the burr hole.

17. The device of claim 12, wherein the base comprises an outer wall and two arcuate beams, each arcuate beam having a fixed end attached to the outer wall of the base, and a free end comprising the clamping wall; the arcuate beam further comprising an inner arcuate surface; wherein the inner arcuate surface and the opposing actuation surface of the clamping wall define the aperture for receiving a respective actuating tab of the interposer.

18. The device of claim 17 wherein the base further comprises a top inside wall and the arcuate beam has an upwardly extended width portion, wherein the opposing surfaces of the top inside wall and the upwardly extended width portion form at least one peripheral lead retention groove.

19. The device of claim 12 wherein the base comprises: an elongated upper body having end portions configured to seat on a cranial surface; two double-ended beams, each double-ended beam having fixed ends attached to respective end portions of the base, wherein each double-ended beam has the clamping wall at its midsection, the clamping walls being recessed inwardly to form the slot for receiving the lead, and having a downward extensions configured to be accommodated in the burr hole; each aperture being formed by the actuation surface and an inside wall of the burr hole;

the base further comprising two middle beams, each middle beam having an upper portion attached to a respective end portion of the base, and an angled end extending downwardly into the burr hole and configured to locate the base in the burr hole.

20. The device of claim 19 wherein each actuating tab comprises a resilient retention tab configured to create an interference fit against the inside wall of the burr hole.

21. The device of claim 19 wherein each angled end of the middle beam comprises protrusions configured to create an interference fit against the inside wall of the burr hole.

22. The device of claim 19 wherein the upper portion of each middle beam comprises a radial lead retention groove extending through the end portion of the base and configured to retentively secure the lead exiting the clamp.

23. The device of claim 19 wherein each end portion of the base further comprises a mounting hole and at least one peripheral lead retention groove.

24. The device of claim 12 further including a cover having retention tabs, wherein the plunger comprises holes for receiving the retention tabs, wherein when the cover tabs are received in the respective holes, the cover is retained on the plunger.

25. The device of claim 24 wherein the cover further comprises a peripheral protrusion following the outline of peripheral lead retention grooves.

26. The device of claim 12 wherein the clamping walls are configured to be normally closed, and wherein a temporary insert is used to spread the clamping walls to allow unimpeded implantation of the lead; wherein after the lead is implanted the insert is removed thus activating the clamp.

27. The device of claim 12 further including a cannula, wherein the clamp is activated on the cannula positioned in the slot, and wherein the clamping action is transferred to the lead after the cannula is retracted from the slot.

* * * * *